US008540977B2

(12) United States Patent
Baca

(10) Patent No.: US 8,540,977 B2

(45) **Date of Patent: *Sep. 24, 2013**

(54) IL-11 MUTEINS

(75) Inventor: Manuel Baca, Gaithersburg, MD (US)

(73) Assignee: CSL Limited, Parkville, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/189,850

(22) Filed: Jul. 25, 2011

(65) Prior Publication Data

US 2011/0300100 A1 Dec. 8, 2011

Related U.S. Application Data

(63) Continuation of application No. 12/257,565, filed on Oct. 24, 2008, now Pat. No. 7,993,637.

(60) Provisional application No. 61/000,576, filed on Oct. 26, 2007.

(51) Int. Cl.

*C07K 14/54* (2006.01)

*A61K 38/20* (2006.01)

(52) U.S. Cl.

USPC ......... 424/85.2; 424/85.1; 514/21.2; 530/402

(58) Field of Classification Search

None

See application file for complete search history.

(56) References Cited

U.S. PATENT DOCUMENTS 7,495,087 B2 2/2009 Cox, III 7,993,637 B2 * 8/2011 Baca ............................ 424/85.2

FOREIGN PATENT DOCUMENTS

WO WO 03/099322 A2 12/2003

WO WO 2005/014643 A2 2/2005

OTHER PUBLICATIONS

Mikayama et al. Proc. Natl. Acad. Sci. USA, vol. 90, pp. 10056-10060 (1993).*

Voet et al. Biochemistry John Wiley & Sons, Inc., pp. 126-128 and 228-234 (1990).*

Czupryn, M., et al., "Alanine-scanning Mutagenesis of Human Interleukin-11: Identification of Regions Important for Biological Activity", Annals of the New York Academy of Sciences, vol. 762, pp. 152-164 (1995).

Barton, V., et al. "Identification of Three Distinct Receptor Binding Sites of Murine Interleukin-11", Journal of Biological Chemistry, American Society for Biochemistry and Molecular Biology, Inc., U.S., vol. 274, No. 9, pp. 5755-5761 (1999).

Tacken, I., et al., "Definition of receptor binding sites on human interleukin-11 by molecular modeling-guided mutagenesis", European Journal of Biochemistry, vol. 265, No. 2, pp. 645-655 (1999).

International Search Report mailed Jan. 7, 2009 in connection with PCT International Application No. PCT/AU2008/001587 filed Oct. 24, 2008.

Extended European Search Report dated Dec. 30, 2010 in connection with European Patent Application No. 08842066.

Nicholas Underhill-Day et al., "Functional Characterization of W147A: A High-Affinity Interleukin-11 Antagonist," Endocrinology 144(8):3406-14 (2003).

Harmegnies, D., et al., "Characterization of a potent human interleukin-11 agonist", Biochem. J. 375:23-32 (2003).

Yanaka, S. et al., "Non-core Region Modulates Interleukin-11 Signaling Activity Generation of Agonist and Antagonist Variants", The Journal of Biological Chemistry, 286(10):8085-8093 (Mar. 11, 2011) together with Supplemental Information, pp. S1-S6.

* cited by examiner

*Primary Examiner* — Prema Mertz

(74) *Attorney, Agent, or Firm* — Scully, Scott, Murphy & Presser, P.C.

(57) ABSTRACT

The present invention relates generally to the treatment of an interleukin-11 (IL-11)-mediated condition. More particularly, the present invention provides the use of modified forms of IL-11 which modulate IL-11 signaling in the treatment of IL-11-mediated conditions.

12 Claims, 7 Drawing Sheets

Human: Mature IL-11 Sequence

(SEQ ID NO:1)

PGPPPGPPRV.SPDPRAELDS.TVLLTRSLLA.DTRQLAAQLR.DKFPADGDHN.LDSLPTLAMS
AGALGALQLP GVLTRLRADL LSYLRHVQWL RRAGGSSLKT LEPELGTLQA RLDRLLRRLQ
LLMSRLALPQ PPPDPPAPPL APPSSAWGGI RAAHAILGGL HLTLDWAVRG LLLLKTRL

Murine: Mature IL-11 Sequence

(SEQ ID NO:2)

PGPPAGSPRV SSDPRADLDS AVLLTRSLLA DTRQLAAQMR DKFPADGDHS LDSLPTLAMS
AGTLGSLQLP GVLTRLRVDL MSYLRHVQWL RRAGGPSLKT LEPELGALQA RLERLLRRLQ
LLMSRLALPQ AAPDQPVIPL GPPASAWGSI RAAHAILGGL HLTLDWAVRG LLLLKTRL

Macaque: Mature IL-11 Sequence

(SEQ ID NO:3)

PGPPPGSPRA SPDPRAELDS TVLLTRSLLE DTRQLTIQLK DKFPADGDHN LDSLPTLAMS
AGALGALQLP SVLTRLRADL LSYLRHVQWL RRAMGSSLKT LEPELGTLQT RLDRLLRRLQ
LLMSRLALPQ LPPDPPAPPL APPSSTWGGI RAAHAILGGL HLTLDWAVRG LLLLKTRL

Figure 1a

Macaque: PAIDY IL-11 Sequence

(SEQ ID NO:4)

PGPPPGSPRA SPDPRAELDS TVLLTRSLLE DTRQLTIQLK DKFPADGDHN LDSLPTLPAI
DYALGALQLP SVLTRLRADL LSYLRHVQWL RRAMGSSLKT LEPELGTLQT RLDRLLRRLQ
LLMSRLALPQ LPPDPPAPPL APPSSTWGGI RAAHAILGGL HLTLDWAVRG LLLLKTRL

Human: PAIDY IL-11 Mutein

(SEQ ID NO:5)

PGPPPGPPRV.SPDPRAELDS.TVLLTRSLLA.DTRQLAAQLR.DKFPADGDHN.LDSLPTLPAI
DYALGALQLP GVLTRLRADL LSYLRHVQWL RRAGGSSLKT LEPELGTLQA RLDRLLRRLQ
LLMSRLALPQ PPPDPPAPPL APPSSAWGGI RAAHAILGGL HLTLDWAVRG LLLLKTRL

Murine: PAIDY IL-11 Mutein

(SEQ ID NO:6)

PGPPAGSPRV SSDPRADLDS AVLLTRSLLA DTRQLAAQMR DKFPADGDHS LDSLPTLPAI
DYTLGSLQLP GVLTRLRVDL MSYLRHVQWL RRAGGPSLKT LEPELGALQA RLERLLRRLQ
LLMSRLALPQ AAPDQPVIPL GPPASAWGSI RAAHAILGGL HLTLDWAVRG LLLLKTRL

Figure 1b

Human: FMQIQ IL-11 Mutein

(SEQ ID NO:7)

PGPPPGPPRV.SPDPRAELDS.TVLLTRSLLA.DTRQLAAQLR.DKFPADGDHN.LDSLPTLFMQ
IQALGALQLP GVLTRLRADL LSYLRHVQWL RRAGGSSLKT LEPELGTLQA RLDRLLRRLQ
LLMSRLALPQ PPPDPPAPPL APPSSAWGGI RAAHAILGGL HLTLDWAVRG LLLLKTRL

Murine: FMQIQ IL-11 Mutein

(SEQ ID NO:8)

PGPPAGSPRV SSDPRADLDS AVLLTRSLLA DTRQLAAQMR DKFPADGDHS LDSLPTLFMQ
IQTLGSLQLP GVLTRLRVDL MSYLRHVQWL RRAGGPSLKT LEPELGALQA RLERLLRRLQ
LLMSRLALPQ AAPDQPVIPL GPPASAWGSI RAAHAILGGL HLTLDWAVRG LLLLKTRL

Macaque: FMQIQ IL-11 Sequence

(SEQ ID NO:13)

PGPPPGSPRA SPDPRAELDS TVLLTRSLLE DTRQLTIQLK DKFPADGDHN LDSLPTLFMQ
IQALGALQLP SVLTRLRADL LSYLRHVQWL RRAMGSSLKT LEPELGTLQT RLDRLLRRLQ
LLMSRLALPQ LPPDPPAPPL APPSSTWGGI RAAHAILGGL HLTLDWAVRG LLLLKTRL

Figure 1c

Human: PAIDY & W147A IL-11 Mutein

(SEQ ID NO:9)

PGPPPGPPRV.SPDPRAELDS.TVLLTRSLLA.DTRQLAAQLR.DKFPADGDHN.LDSLPTLPAI
DYALGALQLP GVLTRLRADL LSYLRHVQWL RRAGGSSLKT LEPELGTLQA RLDRLLRRLQ
LLMSRLALPQ PPPDPPAPPL APPSSAAGGI RAAHAILGGL HLTLDWAVRG LLLLKTRL

Murine: PAIDY & W147A IL-11 Mutein

(SEQ ID NO:10)

PGPPAGSPRV SSDPRADLDS AVLLTRSLLA DTRQLAAQMR DKFPADGDHS LDSLPTLPAI
DYTLGSLQLP GVLTRLRVDL MSYLRHVQWL RRAGGPSLKT LEPELGALQA RLERLLRRLQ
LLMSRLALPQ AAPDQPVIPL GPPASAAGSI RAAHAILGGL HLTLDWAVRG LLLLKTRL

Macaque: PAIDY & W147A IL-11 Sequence

(SEQ ID NO:14)

PGPPPGSPRA SPDPRAELDS TVLLTRSLLE DTRQLTIQLK DKFPADGDHN LDSLPTLPAI
DYALGALQLP SVLTRLRADL LSYLRHVQWL RRAMGSSLKT LEPELGTLQT RLDRLLRRLQ
LLMSRLALPQ LPPDPPAPPL APPSSTAGGI RAAHAILGGL HLTLDWAVRG LLLLKTRL

Figure 1d

Human: PAIDY & W147C IL-11 Mutein

(SEQ ID NO:11)

PGPPPGPPRV.SPDPRAELDS.TVLLTRSLLA.DTRQLAAQLR.DKFPADGDHN.LDSLPTLPAI
DYALGALQLP GVLTRLRADL LSYLRHVQWL RRAGGSSLKT LEPELGTLQA RLDRLLRRLQ
LLMSRLALPQ PPPDPPAPPL APPSSACGGI RAAHAILGGL HLTLDWAVRG LLLLKTRL

Murine: PAIDY & W147C IL-11 Mutein

(SEQ ID NO:12)

PGPPAGSPRV SSDPRADLDS AVLLTRSLLA DTRQLAAQMR DKFPADGDHS LDSLPTLPAI
DYTLGSLQLP GVLTRLRVDL MSYLRHVQWL RRAGGPSLKT LEPELGALQA RLERLLRRLQ
LLMSRLALPQ AAPDQPVIPL GPPASACGSI RAAHAILGGL HLTLDWAVRG LLLLKTRL

Macaque: PAIDY & W147C IL-11 Sequence

(SEQ ID NO:15)

PGPPPGSPRA SPDPRAELDS TVLLTRSLLE DTRQLTIQLK DKFPADGDHN LDSLPTLPAI
DYALGALQLP SVLTRLRADL LSYLRHVQWL RRAMGSSLKT LEPELGTLQT RLDRLLRRLQ
LLMSRLALPQ LPPDPPAPPL APPSSTCGGI RAAHAILGGL HLTLDWAVRG LLLLKTRL

Figure 1e

Human: FMQIQ & W147A IL-11 Mutein

(SEQ ID NO:16)

PGPPPGPPRV.SPDPRAELDS.TVLLTRSLLA.DTRQLAAQLR.DKFPADGDHN.LDSLPTLFMQ
IQALGALQLP GVLTRLRADL LSYLRHVQWL RRAGGSSLKT LEPELGTLQA RLDRLLRRLQ
LLMSRLALPQ PPPDPPAPPL APPSSAAGGI RAAHAILGGL HLTLDWAVRG LLLLKTRL

Murine: FMQIQ & W147A IL-11 Mutein

(SEQ ID NO:17)

PGPPAGSPRV SSDPRADLDS AVLLTRSLLA DTRQLAAQMR DKFPADGDHS LDSLPTLFMQ
IQTLGSLQLP GVLTRLRVDL MSYLRHVQWL RRAGGPSLKT LEPELGALQA RLERLLRRLQ
LLMSRLALPQ AAPDQPVIPL GPPASAAGSI RAAHAILGGL HLTLDWAVRG LLLLKTRL

Macaque: FMQIQ & W147A IL-11 Sequence

(SEQ ID NO:18)

PGPPPGSPRA SPDPRAELDS TVLLTRSLLE DTRQLTIQLK DKFPADGDHN LDSLPTLFMQ
IQALGALQLP SVLTRLRADL LSYLRHVQWL RRAMGSSLKT LEPELGTLQT RLDRLLRRLQ
LLMSRLALPQ LPPDPPAPPL APPSSTAGGI RAAHAILGGL HLTLDWAVRG LLLLKTRL

Figure 1f

Human: FMQIQ & W147C IL-11 Mutein

(SEQ ID NO:19)

PGPPPGPPRV.SPDPRAELDS.TVLLTRSLLA.DTRQLAAQLR.DKFPADGDHN.LDSLPTLFMQ
IQALGALQLP GVLTRLRADL LSYLRHVQWL RRAGGSSLKT LEPELGTLQA RLDRLLRRLQ
LLMSRLALPQ PPPDPPAPPL APPSSACGGI RAAHAILGGL HLTLDWAVRG LLLLKTRL

Murine: FMQIQ & W147C IL-11 Mutein

(SEQ ID NO:20)

PGPPAGSPRV SSDPRADLDS AVLLTRSLLA DTRQLAAQMR DKFPADGDHS LDSLPTLFMQ
IQTLGSLQLP GVLTRLRVDL MSYLRHVQWL RRAGGPSLKT LEPELGALQA RLERLLRRLQ
LLMSRLALPQ AAPDQPVIPL GPPASACGSI RAAHAILGGL HLTLDWAVRG LLLLKTRL

Macaque: FMQIQ & W147C IL-11 Sequence

(SEQ ID NO:21)

PGPPPGSPRA SPDPRAELDS TVLLTRSLLE DTRQLTIQLK DKFPADGDHN LDSLPTLFMQ
IQALGALQLP SVLTRLRADL LSYLRHVQWL RRAMGSSLKT LEPELGTLQT RLDRLLRRLQ
LLMSRLALPQ LPPDPPAPPL APPSSTCGGI RAAHAILGGL HLTLDWAVRG LLLLKTRL

Human: N-terminally tagged PAIDY & W147C IL-11 Sequence

(SEQ ID NO:22)

MGSHHHHHHG ARQPGPPPGP PRVSPDPRAE LDSTVLLTRS LLADTRQLAA QLRDKFPADG
DHNLDSLPTL PAIDYALGAL QLPGVLTRLR ADLLSYLRHV QWLRRAGGSS LKTLEPELGT
LQARLDRLLR RLQLLMSRLA LPQPPPDPPA PPLAPPSSAC GGIRAAHAIL GGLHLTLDWA
VRGLLLLKTR L

Figure 1g

SEQUENCE LISTING

```
<160> NUMBER OF SEQ ID NOS: 25

<210> SEQ ID NO 1
<211> LENGTH: 178
<212> TYPE: PRT
<213> ORGANISM: Homo sapiens

<400> SEQUENCE: 1

Pro Gly Pro Pro Pro Gly Pro Pro Arg Val Ser Pro Asp Pro Arg Ala
1               5                   10                  15

Glu Leu Asp Ser Thr Val Leu Leu Thr Arg Ser Leu Leu Ala Asp Thr
            20                  25                  30

Arg Gln Leu Ala Ala Gln Leu Arg Asp Lys Phe Pro Ala Asp Gly Asp
        35                  40                  45

His Asn Leu Asp Ser Leu Pro Thr Leu Ala Met Ser Ala Gly Ala Leu
    50                  55                  60

Gly Ala Leu Gln Leu Pro Gly Val Leu Thr Arg Leu Arg Ala Asp Leu
65                  70                  75                  80

Leu Ser Tyr Leu Arg His Val Gln Trp Leu Arg Arg Ala Gly Gly Ser
                85                  90                  95

Ser Leu Lys Thr Leu Glu Pro Glu Leu Gly Thr Leu Gln Ala Arg Leu
```

-continued

```
            100                 105                 110

Asp Arg Leu Leu Arg Arg Leu Gln Leu Leu Met Ser Arg Leu Ala Leu
        115                 120                 125

Pro Gln Pro Pro Pro Asp Pro Pro Ala Pro Pro Leu Ala Pro Pro Ser
    130                 135                 140

Ser Ala Trp Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 2
<211> LENGTH: 178
<212> TYPE: PRT
<213> ORGANISM: Mus musculus

<400> SEQUENCE: 2

Pro Gly Pro Pro Ala Gly Ser Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Ala Met Ser Ala Gly Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Trp Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 3
<211> LENGTH: 178
<212> TYPE: PRT
<213> ORGANISM: M. mulatta

<400> SEQUENCE: 3

Pro Gly Pro Pro Pro Gly Ser Pro Arg Ala Ser Pro Asp Pro Arg Ala
1               5                   10                  15

Glu Leu Asp Ser Thr Val Leu Leu Thr Arg Ser Leu Leu Glu Asp Thr
            20                  25                  30

Arg Gln Leu Thr Ile Gln Leu Lys Asp Lys Phe Pro Ala Asp Gly Asp
        35                  40                  45

His Asn Leu Asp Ser Leu Pro Thr Leu Ala Met Ser Ala Gly Ala Leu
    50                  55                  60

Gly Ala Leu Gln Leu Pro Ser Val Leu Thr Arg Leu Arg Ala Asp Leu
```

-continued

```
65                  70                  75                  80

Leu Ser Tyr Leu Arg His Val Gln Trp Leu Arg Arg Ala Met Gly Ser
                85                  90                  95

Ser Leu Lys Thr Leu Glu Pro Glu Leu Gly Thr Leu Gln Thr Arg Leu
            100                 105                 110

Asp Arg Leu Leu Arg Arg Leu Gln Leu Leu Met Ser Arg Leu Ala Leu
        115                 120                 125

Pro Gln Leu Pro Pro Asp Pro Pro Ala Pro Pro Leu Ala Pro Pro Ser
    130                 135                 140

Ser Thr Trp Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 4
<211> LENGTH: 178
<212> TYPE: PRT
<213> ORGANISM: M. mulatta

<400> SEQUENCE: 4

Pro Gly Pro Pro Pro Gly Ser Pro Arg Ala Ser Pro Asp Pro Arg Ala
1               5                   10                  15

Glu Leu Asp Ser Thr Val Leu Leu Thr Arg Ser Leu Leu Glu Asp Thr
            20                  25                  30

Arg Gln Leu Thr Ile Gln Leu Lys Asp Lys Phe Pro Ala Asp Gly Asp
        35                  40                  45

His Asn Leu Asp Ser Leu Pro Thr Leu Pro Ala Ile Asp Tyr Ala Leu
    50                  55                  60

Gly Ala Leu Gln Leu Pro Ser Val Leu Thr Arg Leu Arg Ala Asp Leu
65                  70                  75                  80

Leu Ser Tyr Leu Arg His Val Gln Trp Leu Arg Arg Ala Met Gly Ser
                85                  90                  95

Ser Leu Lys Thr Leu Glu Pro Glu Leu Gly Thr Leu Gln Thr Arg Leu
            100                 105                 110

Asp Arg Leu Leu Arg Arg Leu Gln Leu Leu Met Ser Arg Leu Ala Leu
        115                 120                 125

Pro Gln Leu Pro Pro Asp Pro Pro Ala Pro Pro Leu Ala Pro Pro Ser
    130                 135                 140

Ser Thr Trp Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 5
<211> LENGTH: 178
<212> TYPE: PRT
<213> ORGANISM: Homo sapiens

<400> SEQUENCE: 5

Pro Gly Pro Pro Pro Gly Pro Pro Arg Val Ser Pro Asp Pro Arg Ala
1               5                   10                  15

Glu Leu Asp Ser Thr Val Leu Leu Thr Arg Ser Leu Leu Ala Asp Thr
            20                  25                  30

Arg Gln Leu Ala Ala Gln Leu Arg Asp Lys Phe Pro Ala Asp Gly Asp
```

-continued

```
        35                  40                  45

His Asn Leu Asp Ser Leu Pro Thr Leu Pro Ala Ile Asp Tyr Ala Leu
    50                  55                  60

Gly Ala Leu Gln Leu Pro Gly Val Leu Thr Arg Leu Arg Ala Asp Leu
65                  70                  75                  80

Leu Ser Tyr Leu Arg His Val Gln Trp Leu Arg Arg Ala Gly Gly Ser
                85                  90                  95

Ser Leu Lys Thr Leu Glu Pro Glu Leu Gly Thr Leu Gln Ala Arg Leu
            100                 105                 110

Asp Arg Leu Leu Arg Arg Leu Gln Leu Leu Met Ser Arg Leu Ala Leu
        115                 120                 125

Pro Gln Pro Pro Pro Asp Pro Pro Ala Pro Pro Leu Ala Pro Pro Ser
    130                 135                 140

Ser Ala Trp Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 6
<211> LENGTH: 178
<212> TYPE: PRT
<213> ORGANISM: Mus musculus

<400> SEQUENCE: 6

Pro Gly Pro Pro Ala Gly Ser Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Pro Ala Ile Asp Tyr Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Trp Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 7
<211> LENGTH: 178
<212> TYPE: PRT
<213> ORGANISM: Homo sapiens

<400> SEQUENCE: 7

Pro Gly Pro Pro Pro Gly Pro Pro Arg Val Ser Pro Asp Pro Arg Ala
```

-continued

```
1               5                   10                  15

Glu Leu Asp Ser Thr Val Leu Leu Thr Arg Ser Leu Leu Ala Asp Thr
            20                  25                  30

Arg Gln Leu Ala Ala Gln Leu Arg Asp Lys Phe Pro Ala Asp Gly Asp
        35                  40                  45

His Asn Leu Asp Ser Leu Pro Thr Leu Phe Met Gln Ile Gln Ala Leu
    50                  55                  60

Gly Ala Leu Gln Leu Pro Gly Val Leu Thr Arg Leu Arg Ala Asp Leu
65                  70                  75                  80

Leu Ser Tyr Leu Arg His Val Gln Trp Leu Arg Arg Ala Gly Gly Ser
                85                  90                  95

Ser Leu Lys Thr Leu Glu Pro Glu Leu Gly Thr Leu Gln Ala Arg Leu
            100                 105                 110

Asp Arg Leu Leu Arg Arg Leu Gln Leu Leu Met Ser Arg Leu Ala Leu
        115                 120                 125

Pro Gln Pro Pro Pro Asp Pro Pro Ala Pro Pro Leu Ala Pro Pro Ser
    130                 135                 140

Ser Ala Trp Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 8
<211> LENGTH: 178
<212> TYPE: PRT
<213> ORGANISM: Mus musculus

<400> SEQUENCE: 8

Pro Gly Pro Pro Ala Gly Ser Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Phe Met Gln Ile Gln Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Trp Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 9
<211> LENGTH: 178
```

<212> TYPE: PRT
<213> ORGANISM: Homo sapiens

<400> SEQUENCE: 9

```
Pro Gly Pro Pro Pro Gly Pro Pro Arg Val Ser Pro Asp Pro Arg Ala
1               5                   10                  15

Glu Leu Asp Ser Thr Val Leu Leu Thr Arg Ser Leu Leu Ala Asp Thr
            20                  25                  30

Arg Gln Leu Ala Ala Gln Leu Arg Asp Lys Phe Pro Ala Asp Gly Asp
        35                  40                  45

His Asn Leu Asp Ser Leu Pro Thr Leu Pro Ala Ile Asp Tyr Ala Leu
    50                  55                  60

Gly Ala Leu Gln Leu Pro Gly Val Leu Thr Arg Leu Arg Ala Asp Leu
65                  70                  75                  80

Leu Ser Tyr Leu Arg His Val Gln Trp Leu Arg Arg Ala Gly Gly Ser
                85                  90                  95

Ser Leu Lys Thr Leu Glu Pro Glu Leu Gly Thr Leu Gln Ala Arg Leu
            100                 105                 110

Asp Arg Leu Leu Arg Arg Leu Gln Leu Leu Met Ser Arg Leu Ala Leu
        115                 120                 125

Pro Gln Pro Pro Pro Asp Pro Pro Ala Pro Pro Leu Ala Pro Pro Ser
    130                 135                 140

Ser Ala Ala Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu
```

<210> SEQ ID NO 10
<211> LENGTH: 178
<212> TYPE: PRT
<213> ORGANISM: Mus musculus

<400> SEQUENCE: 10

```
Pro Gly Pro Pro Ala Gly Ser Pro Arg Val Ser Ser Asp Pro Arg Ala
1               5                   10                  15

Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Pro Ala Ile Asp Tyr Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Ala Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175
```

Arg Leu

<210> SEQ ID NO 11
<211> LENGTH: 178
<212> TYPE: PRT
<213> ORGANISM: Homo sapiens

<400> SEQUENCE: 11

Pro Gly Pro Pro Pro Gly Pro Pro Arg Val Ser Pro Asp Pro Arg Ala
1 5 10 15

Glu Leu Asp Ser Thr Val Leu Leu Thr Arg Ser Leu Leu Ala Asp Thr
20 25 30

Arg Gln Leu Ala Ala Gln Leu Arg Asp Lys Phe Pro Ala Asp Gly Asp
35 40 45

His Asn Leu Asp Ser Leu Pro Thr Leu Pro Ala Ile Asp Tyr Ala Leu
50 55 60

Gly Ala Leu Gln Leu Pro Gly Val Leu Thr Arg Leu Arg Ala Asp Leu
65 70 75 80

Leu Ser Tyr Leu Arg His Val Gln Trp Leu Arg Arg Ala Gly Gly Ser
85 90 95

Ser Leu Lys Thr Leu Glu Pro Glu Leu Gly Thr Leu Gln Ala Arg Leu
100 105 110

Asp Arg Leu Leu Arg Arg Leu Gln Leu Leu Met Ser Arg Leu Ala Leu
115 120 125

Pro Gln Pro Pro Pro Asp Pro Pro Ala Pro Pro Leu Ala Pro Pro Ser
130 135 140

Ser Ala Cys Gly Gly Ile Arg Ala Ala His Ala Ile Leu Gly Gly Leu
145 150 155 160

His Leu Thr Leu Asp Trp Ala Val Arg Gly Leu Leu Leu Leu Lys Thr
165 170 175

Arg Leu

<210> SEQ ID NO 12
<211> LENGTH: 178
<212> TYPE: PRT
<213> ORGANISM: Mus musculus

<400> SEQUENCE: 12

Pro Gly Pro Pro Ala Gly Ser Pro Arg Val Ser Ser Asp Pro Arg Ala
1 5 10 15

Asp Leu Asp Ser Ala Val Leu Leu Thr Arg Ser Leu Leu Ala Asp Thr
20 25 30

Arg Gln Leu Ala Ala Gln Met Arg Asp Lys Phe Pro Ala Asp Gly Asp
35 40 45

His Ser Leu Asp Ser Leu Pro Thr Leu Pro Ala Ile Asp Tyr Thr Leu
50 55 60

Gly Ser Leu Gln Leu Pro Gly Val Leu Thr Arg Leu Arg Val Asp Leu
65 70 75 80

Met Ser Tyr Leu Arg His Val Gln Trp Leu Arg Arg Ala Gly Gly Pro
85 90 95

Ser Leu Lys Thr Leu Glu Pro Glu Leu Gly Ala Leu Gln Ala Arg Leu
100 105 110

Glu Arg Leu Leu Arg Arg Leu Gln Leu Leu Met Ser Arg Leu Ala Leu
115 120 125

Pro Gln Ala Ala Pro Asp Gln Pro Val Ile Pro Leu Gly Pro Pro Ala
130 135 140

Ser Ala Cys Gly Ser Ile Arg Ala Ala His Ala Ile Leu Gly Gly Leu
145 150 155 160

His Leu Thr Leu Asp Trp Ala Val Arg Gly Leu Leu Leu Leu Lys Thr
165 170 175

Arg Leu

<210> SEQ ID NO 13
<211> LENGTH: 178
<212> TYPE: PRT
<213> ORGANISM: M. mulatta

<400> SEQUENCE: 13

Pro Gly Pro Pro Pro Gly Ser Pro Arg Ala Ser Pro Asp Pro Arg Ala
1 5 10 15

Glu Leu Asp Ser Thr Val Leu Leu Thr Arg Ser Leu Leu Glu Asp Thr
20 25 30

Arg Gln Leu Thr Ile Gln Leu Lys Asp Lys Phe Pro Ala Asp Gly Asp
35 40 45

His Asn Leu Asp Ser Leu Pro Thr Leu Phe Met Gln Ile Gln Ala Leu
50 55 60

Gly Ala Leu Gln Leu Pro Ser Val Leu Thr Arg Leu Arg Ala Asp Leu
65 70 75 80

Leu Ser Tyr Leu Arg His Val Gln Trp Leu Arg Arg Ala Met Gly Ser
85 90 95

Ser Leu Lys Thr Leu Glu Pro Glu Leu Gly Thr Leu Gln Thr Arg Leu
100 105 110

Asp Arg Leu Leu Arg Arg Leu Gln Leu Leu Met Ser Arg Leu Ala Leu
115 120 125

Pro Gln Leu Pro Pro Asp Pro Pro Ala Pro Pro Leu Ala Pro Pro Ser
130 135 140

Ser Thr Trp Gly Gly Ile Arg Ala Ala His Ala Ile Leu Gly Gly Leu
145 150 155 160

His Leu Thr Leu Asp Trp Ala Val Arg Gly Leu Leu Leu Leu Lys Thr
165 170 175

Arg Leu

<210> SEQ ID NO 14
<211> LENGTH: 178
<212> TYPE: PRT
<213> ORGANISM: M. mulatta

<400> SEQUENCE: 14

Pro Gly Pro Pro Pro Gly Ser Pro Arg Ala Ser Pro Asp Pro Arg Ala
1 5 10 15

Glu Leu Asp Ser Thr Val Leu Leu Thr Arg Ser Leu Leu Glu Asp Thr
20 25 30

Arg Gln Leu Thr Ile Gln Leu Lys Asp Lys Phe Pro Ala Asp Gly Asp
35 40 45

His Asn Leu Asp Ser Leu Pro Thr Leu Pro Ala Ile Asp Tyr Ala Leu
50 55 60

Gly Ala Leu Gln Leu Pro Ser Val Leu Thr Arg Leu Arg Ala Asp Leu
65 70 75 80

Leu Ser Tyr Leu Arg His Val Gln Trp Leu Arg Arg Ala Met Gly Ser
85 90 95

Ser Leu Lys Thr Leu Glu Pro Glu Leu Gly Thr Leu Gln Thr Arg Leu
100 105 110

```
Asp Arg Leu Leu Arg Arg Leu Gln Leu Leu Met Ser Arg Leu Ala Leu
        115                 120                 125

Pro Gln Leu Pro Pro Asp Pro Pro Ala Pro Pro Leu Ala Pro Pro Ser
    130                 135                 140

Ser Thr Ala Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 15
<211> LENGTH: 178
<212> TYPE: PRT
<213> ORGANISM: M. mulatta

<400> SEQUENCE: 15

Pro Gly Pro Pro Pro Gly Ser Pro Arg Ala Ser Pro Asp Pro Arg Ala
1               5                   10                  15

Glu Leu Asp Ser Thr Val Leu Leu Thr Arg Ser Leu Leu Glu Asp Thr
            20                  25                  30

Arg Gln Leu Thr Ile Gln Leu Lys Asp Lys Phe Pro Ala Asp Gly Asp
        35                  40                  45

His Asn Leu Asp Ser Leu Pro Thr Leu Pro Ala Ile Asp Tyr Ala Leu
    50                  55                  60

Gly Ala Leu Gln Leu Pro Ser Val Leu Thr Arg Leu Arg Ala Asp Leu
65                  70                  75                  80

Leu Ser Tyr Leu Arg His Val Gln Trp Leu Arg Arg Ala Met Gly Ser
                85                  90                  95

Ser Leu Lys Thr Leu Glu Pro Glu Leu Gly Thr Leu Gln Thr Arg Leu
            100                 105                 110

Asp Arg Leu Leu Arg Arg Leu Gln Leu Leu Met Ser Arg Leu Ala Leu
        115                 120                 125

Pro Gln Leu Pro Pro Asp Pro Pro Ala Pro Pro Leu Ala Pro Pro Ser
    130                 135                 140

Ser Thr Cys Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 16
<211> LENGTH: 178
<212> TYPE: PRT
<213> ORGANISM: Homo sapiens

<400> SEQUENCE: 16

Pro Gly Pro Pro Pro Gly Pro Pro Arg Val Ser Pro Asp Pro Arg Ala
1               5                   10                  15

Glu Leu Asp Ser Thr Val Leu Leu Thr Arg Ser Leu Leu Ala Asp Thr
            20                  25                  30

Arg Gln Leu Ala Ala Gln Leu Arg Asp Lys Phe Pro Ala Asp Gly Asp
        35                  40                  45

His Asn Leu Asp Ser Leu Pro Thr Leu Phe Met Gln Ile Gln Ala Leu
    50                  55                  60

Gly Ala Leu Gln Leu Pro Gly Val Leu Thr Arg Leu Arg Ala Asp Leu
65                  70                  75                  80
```

Leu Ser Tyr Leu Arg His Val Gln Trp Leu Arg Arg Ala Gly Gly Ser
85 90 95

Ser Leu Lys Thr Leu Glu Pro Glu Leu Gly Thr Leu Gln Ala Arg Leu
100 105 110

Asp Arg Leu Leu Arg Arg Leu Gln Leu Leu Met Ser Arg Leu Ala Leu
115 120 125

Pro Gln Pro Pro Pro Asp Pro Pro Ala Pro Pro Leu Ala Pro Pro Ser
130 135 140

Ser Ala Ala Gly Gly Ile Arg Ala Ala His Ala Ile Leu Gly Gly Leu
145 150 155 160

His Leu Thr Leu Asp Trp Ala Val Arg Gly Leu Leu Leu Leu Lys Thr
165 170 175

Arg Leu

<210> SEQ ID NO 17
<211> LENGTH: 178
<212> TYPE: PRT
<213> ORGANISM: Mus musculus

<400> SEQUENCE: 17

Pro Gly Pro Pro Ala Gly Ser Pro Arg Val Ser Ser Asp Pro Arg Ala
1 5 10 15

Asp Leu Asp Ser Ala Val Leu Leu Thr Arg Ser Leu Leu Ala Asp Thr
20 25 30

Arg Gln Leu Ala Ala Gln Met Arg Asp Lys Phe Pro Ala Asp Gly Asp
35 40 45

His Ser Leu Asp Ser Leu Pro Thr Leu Phe Met Gln Ile Gln Thr Leu
50 55 60

Gly Ser Leu Gln Leu Pro Gly Val Leu Thr Arg Leu Arg Val Asp Leu
65 70 75 80

Met Ser Tyr Leu Arg His Val Gln Trp Leu Arg Arg Ala Gly Gly Pro
85 90 95

Ser Leu Lys Thr Leu Glu Pro Glu Leu Gly Ala Leu Gln Ala Arg Leu
100 105 110

Glu Arg Leu Leu Arg Arg Leu Gln Leu Leu Met Ser Arg Leu Ala Leu
115 120 125

Pro Gln Ala Ala Pro Asp Gln Pro Val Ile Pro Leu Gly Pro Pro Ala
130 135 140

Ser Ala Ala Gly Ser Ile Arg Ala Ala His Ala Ile Leu Gly Gly Leu
145 150 155 160

His Leu Thr Leu Asp Trp Ala Val Arg Gly Leu Leu Leu Leu Lys Thr
165 170 175

Arg Leu

<210> SEQ ID NO 18
<211> LENGTH: 178
<212> TYPE: PRT
<213> ORGANISM: M. mulatta

<400> SEQUENCE: 18

Pro Gly Pro Pro Pro Gly Ser Pro Arg Ala Ser Pro Asp Pro Arg Ala
1 5 10 15

Glu Leu Asp Ser Thr Val Leu Leu Thr Arg Ser Leu Leu Glu Asp Thr
20 25 30

Arg Gln Leu Thr Ile Gln Leu Lys Asp Lys Phe Pro Ala Asp Gly Asp
35 40 45

```
His Asn Leu Asp Ser Leu Pro Thr Leu Phe Met Gln Ile Gln Ala Leu
    50                  55                  60

Gly Ala Leu Gln Leu Pro Ser Val Leu Thr Arg Leu Arg Ala Asp Leu
65                  70                  75                  80

Leu Ser Tyr Leu Arg His Val Gln Trp Leu Arg Arg Ala Met Gly Ser
                85                  90                  95

Ser Leu Lys Thr Leu Glu Pro Glu Leu Gly Thr Leu Gln Thr Arg Leu
            100                 105                 110

Asp Arg Leu Leu Arg Arg Leu Gln Leu Leu Met Ser Arg Leu Ala Leu
        115                 120                 125

Pro Gln Leu Pro Pro Asp Pro Pro Ala Pro Pro Leu Ala Pro Pro Ser
    130                 135                 140

Ser Thr Ala Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 19
<211> LENGTH: 178
<212> TYPE: PRT
<213> ORGANISM: Homo sapiens

<400> SEQUENCE: 19

Pro Gly Pro Pro Pro Gly Pro Pro Arg Val Ser Pro Asp Pro Arg Ala
1               5                   10                  15

Glu Leu Asp Ser Thr Val Leu Leu Thr Arg Ser Leu Leu Ala Asp Thr
            20                  25                  30

Arg Gln Leu Ala Ala Gln Leu Arg Asp Lys Phe Pro Ala Asp Gly Asp
        35                  40                  45

His Asn Leu Asp Ser Leu Pro Thr Leu Phe Met Gln Ile Gln Ala Leu
    50                  55                  60

Gly Ala Leu Gln Leu Pro Gly Val Leu Thr Arg Leu Arg Ala Asp Leu
65                  70                  75                  80

Leu Ser Tyr Leu Arg His Val Gln Trp Leu Arg Arg Ala Gly Gly Ser
                85                  90                  95

Ser Leu Lys Thr Leu Glu Pro Glu Leu Gly Thr Leu Gln Ala Arg Leu
            100                 105                 110

Asp Arg Leu Leu Arg Arg Leu Gln Leu Leu Met Ser Arg Leu Ala Leu
        115                 120                 125

Pro Gln Pro Pro Pro Asp Pro Pro Ala Pro Pro Leu Ala Pro Pro Ser
    130                 135                 140

Ser Ala Cys Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 20
<211> LENGTH: 178
<212> TYPE: PRT
<213> ORGANISM: Mus musculus

<400> SEQUENCE: 20

Pro Gly Pro Pro Ala Gly Ser Pro Arg Val Ser Ser Asp Pro Arg Ala
1               5                   10                  15
```

```
Asp Leu Asp Ser Ala Val Leu Leu Thr Arg Ser Leu Leu Ala Asp Thr
            20                  25                  30

Arg Gln Leu Ala Ala Gln Met Arg Asp Lys Phe Pro Ala Asp Gly Asp
        35                  40                  45

His Ser Leu Asp Ser Leu Pro Thr Leu Phe Met Gln Ile Gln Thr Leu
    50                  55                  60

Gly Ser Leu Gln Leu Pro Gly Val Leu Thr Arg Leu Arg Val Asp Leu
65                  70                  75                  80

Met Ser Tyr Leu Arg His Val Gln Trp Leu Arg Arg Ala Gly Gly Pro
                85                  90                  95

Ser Leu Lys Thr Leu Glu Pro Glu Leu Gly Ala Leu Gln Ala Arg Leu
            100                 105                 110

Glu Arg Leu Leu Arg Arg Leu Gln Leu Leu Met Ser Arg Leu Ala Leu
        115                 120                 125

Pro Gln Ala Ala Pro Asp Gln Pro Val Ile Pro Leu Gly Pro Pro Ala
    130                 135                 140

Ser Ala Cys Gly Ser Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 21
<211> LENGTH: 178
<212> TYPE: PRT
<213> ORGANISM: M. mulatta

<400> SEQUENCE: 21

Pro Gly Pro Pro Pro Gly Ser Pro Arg Ala Ser Pro Asp Pro Arg Ala
1               5                   10                  15

Glu Leu Asp Ser Thr Val Leu Leu Thr Arg Ser Leu Leu Glu Asp Thr
            20                  25                  30

Arg Gln Leu Thr Ile Gln Leu Lys Asp Lys Phe Pro Ala Asp Gly Asp
        35                  40                  45

His Asn Leu Asp Ser Leu Pro Thr Leu Phe Met Gln Ile Gln Ala Leu
    50                  55                  60

Gly Ala Leu Gln Leu Pro Ser Val Leu Thr Arg Leu Arg Ala Asp Leu
65                  70                  75                  80

Leu Ser Tyr Leu Arg His Val Gln Trp Leu Arg Arg Ala Met Gly Ser
                85                  90                  95

Ser Leu Lys Thr Leu Glu Pro Glu Leu Gly Thr Leu Gln Thr Arg Leu
            100                 105                 110

Asp Arg Leu Leu Arg Arg Leu Gln Leu Leu Met Ser Arg Leu Ala Leu
        115                 120                 125

Pro Gln Leu Pro Pro Asp Pro Pro Ala Pro Pro Leu Ala Pro Pro Ser
    130                 135                 140

Ser Thr Cys Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu


<210> SEQ ID NO 22
<211> LENGTH: 191
<212> TYPE: PRT
```

<213> ORGANISM: Homo sapiens

<400> SEQUENCE: 22

```
Met Gly Ser His His His His His His Gly Ala Arg Gln Pro Gly Pro
1               5                   10                  15

Pro Pro Gly Pro Pro Arg Val Ser Pro Asp Pro Arg Ala Glu Leu Asp
            20                  25                  30

Ser Thr Val Leu Leu Thr Arg Ser Leu Leu Ala Asp Thr Arg Gln Leu
        35                  40                  45

Ala Ala Gln Leu Arg Asp Lys Phe Pro Ala Asp Gly Asp His Asn Leu
    50                  55                  60

Asp Ser Leu Pro Thr Leu Pro Ala Ile Asp Tyr Ala Leu Gly Ala Leu
65                  70                  75                  80

Gln Leu Pro Gly Val Leu Thr Arg Leu Arg Ala Asp Leu Leu Ser Tyr
                85                  90                  95

Leu Arg His Val Gln Trp Leu Arg Arg Ala Gly Gly Ser Ser Leu Lys
            100                 105                 110

Thr Leu Glu Pro Glu Leu Gly Thr Leu Gln Ala Arg Leu Asp Arg Leu
        115                 120                 125

Leu Arg Arg Leu Gln Leu Leu Met Ser Arg Leu Ala Leu Pro Gln Pro
    130                 135                 140

Pro Pro Asp Pro Pro Ala Pro Pro Leu Ala Pro Pro Ser Ser Ala Cys
145                 150                 155                 160

Gly Gly Ile Arg Ala Ala His Ala Ile Leu Gly Gly Leu His Leu Thr
                165                 170                 175

Leu Asp Trp Ala Val Arg Gly Leu Leu Leu Leu Lys Thr Arg Leu
            180                 185                 190
```

<210> SEQ ID NO 23
<211> LENGTH: 5
<212> TYPE: PRT
<213> ORGANISM: artificial
<220> FEATURE:
<223> OTHER INFORMATION: Amino acid IL-11

<400> SEQUENCE: 23

```
Ala Met Ser Ala Gly
1               5
```

<210> SEQ ID NO 24
<211> LENGTH: 5
<212> TYPE: PRT
<213> ORGANISM: artificial
<220> FEATURE:
<223> OTHER INFORMATION: Amino Acid IL-11

<400> SEQUENCE: 24

```
Pro Ala Ile Asp Tyr
1               5
```

<210> SEQ ID NO 25
<211> LENGTH: 5
<212> TYPE: PRT
<213> ORGANISM: artificial
<220> FEATURE:
<223> OTHER INFORMATION: Amino Acid IL-11

<400> SEQUENCE: 25

```
Phe Met Gln Ile Gln
1               5
```

IL-11 MUTEINS

APPLICATION DATA

This application is a continuation of U.S. Ser. No. 12/257,565, filed on Oct. 24, 2008, which is associated with and claims priority from U.S. Provisional Patent Application No. 61/000,576, filed on 26 Oct., 2007, the entire contents of which are incorporated herein by reference.

FIELD

The present invention relates generally to the treatment of an interleukin-11 (IL-11)-mediated condition. More particularly, the present invention provides the use of modified forms of IL-11 which modulate IL-11 signaling in the treatment of IL-11-mediated conditions.

BACKGROUND

Bibliographic details of references provided in the subject specification are listed at the end of the specification.

Reference to any prior art is not, and should not be taken as an acknowledgment or any form of suggestion that this prior art forms part of the common general knowledge in any country.

Interleukin-11 (IL-11) is a member of the IL-6 family of cytokines which includes IL-6, viral IL-6 (vIL-6), leukemia inhibitory factor (LIF), oncostatin M (OSM), ciliary neutrophic factor (CNTF), cardiotrophin-1 (CT-1), cardiotrophin-like cytokine/cytokine-like factor-1 (CLC/CLF), IL-27 and neuropoietin (NP). IL-11 is able to stimulate the growth and differentiation of various lineages of hematopoietic cells, either alone or in synergy with other cytokines. IL-11 is also able to stimulate megakaryopoiesis and platelet production, and is used clinically to prevent chemotherapy-induced thrombocytopenia (Tepler et al, *Blood* 87(9):3607-3614, 1996) and is currently being assessed as a new approach to the treatment of chemotherapy-induced gastrointestinal mucositis (Herrlinger et al, *Am J Gastroenterol* 101(4):793-797, 2006). IL-11 has also been suggested as being of benefit in arthritis and inflammatory bowel disease.

IL-11 also exerts a variety, of biological activities outside the hematopoietic system. It is a regulator of osteoclast development and believed to be a regulator of bone metabolism (Girasole et al, *J clin Invest* 93:1516-1524, 1994; Hughes et al, *Calcif tissue Int* 53:362-364, 1993; Heymann and Rousselle, *Cytokine* 12(10):1455-1468, 2000). IL-11 is expressed at high levels in cells of the CNS (Du et al, *J Cell Physiol* 168:362-372, 1996) and stimulates the survival and proliferation of neuronal progenitor cells (Mehler et al, *nature* 362:62-65, 1993). In female mice, IL-11 is essential for successful embryo implantation (Dimitriadeis et al, *Mol Hum Reprod.* 6(10):907-914, 2000; Robb et al, *Nat Med* 4:303-308, 1998; Bilinski et al, *Genes Dev* 12:2234-2243, 1998) and the expression pattern of IL-11 and its receptors during the menstrual cycle suggests a similar role in humans. Other non-hematopoietic activities of IL-11 include inhibition of adipogenesis (Ohsumi et al, *FEBS Lett* 288:13-16, 1991; Ohsumi et al, *Biochem Mol Biol Int* 32:705-712, 1994), induction of a febrile response (Lopez-Valpuesta et al, *Neruopharmacology* 33:989-994, 1994), modulation of extracellular matrix metabolism (Maier et al, *J Biol chem.* 268:21527-21532, 1993), stimulation of acute-phase reactants (Baumann and Schendel, *J Biol Chem* 266:20424020427 1991), and proposed pro- and anti-inflammatory roles (Trepicchio et al, *J Clin Invest* 104:1527-1537, 1999; Redlich et al, *J Immunol* 157:1705-1710, 1996).

IL-11 has also been suggested as a potential therapeutic agent in various other inflammatory disorders including radiation-induced lung damage (Redlich et al, supra 1996), sepsis (Chang et al, *Blood Cells Mol Dis* 22(1):57-67, 1996) and psoriasis (Trepicchio et al, supra 1999). U.S. Pat. No. 6,270,759 suggests that IL-11 may be therapeutically useful for a variety of inflammatory conditions including asthma and rhinitis.

Indicative of the therapeutic interest in IL-11, US Patent Application No. 2007/0190024 describes modified forms of IL-11 with mutations at His 182 (H182) and Asp 186 (D186) which act as agonists and hyperagonists of IL-11.

IL-11 exerts its effects via association with a specific cell surface receptor (IL-11Rα) as well as the shared receptor subunit gp130. While all IL-6 family cytokines signal through receptor complexes involving one or more gp130 molecules, the IL-11 signaling complex is most similar to that of IL-6 in that it comprises two molecules each of the cytokine, specific α-chain receptor and gp130 (Barton et al, *J Biol Chem* (2000) 275:36197-36203, 2000).

While neutralizing antibodies and soluble receptor proteins are a common strategy for inhibiting cytokines, a third class of antagonist molecules are referred to as "cytokine muteins" which prevent signaling by binding to only one of the two receptor chains. A number of these muteins has previously been described and one, an antagonistic variant of growth hormone, is used clinically to treat acromegaly (Cunningham and Wells, *Science* 244:1081-1085, 1989). Within the IL-6 family of cytokines, cytokine muteins have been described for IL-6, CNTF, LIF and IL-11 (Ehlers et al, *J Biol Chem* 270:8158-8163, 1995; Brakenhoff et al, *J Biol Chem* 269:86-93, 1994; Savino et al, *Embo J* 13:5863-5870, 1994; Hudson et al, *J Biol Chem* 271:11971-11978, 1996; Saggio et al, *Embo J* 14; 3045-3054, 1995; Underhill-Day et al, *Endocrinology* 144; 3406-3414, 2003). In each case, these cytokine mutein contain specific mutations which prevent binding of cytokine to gp130. In the case of IL-11, a single point mutation, W147A (a tryptophan to alanine substitution at amino acid residue 147), is sufficient to convert IL-11 from an agonist into an antagonist of IL-11 signaling with the affinity for IL-11Rα unchanged (Underhill-Day et al, supra 2003).

In addition, structure-function studies have identified various regions of murine and human IL-11 which are important for IL-11Rα binding (Czupryn et al, *J. Biol. Chem.* 270 (2):978-985, 1995; Miyadai et al, *Biosci. Biotechnol. Biochem.* 60.3:541-542, 1996; Czupryn et al, *Ann. N.Y. Acad. Sci.* 762:152-164, 1995; Tacken et al, *Eur. J. Biochem.* 265.2:645-655, 1999; Harmegnies et al, *Biochem J.* 375(1):23-32, 2003). In particular, residues D165, W166, R169, L172 and L173 at the C-terminal end of the D-helix, and M58, L64 and L67 in the A-B loop were found to contribute to IL-11Rα binding.

US Patent Application No. 2007/0190024 describes IL-11 muteins with mutations at His 182 (H182) and Asp 186 (D186) of IL-11 as agonists and hyperagonists of IL-11, but does not suggest antagonists. The IL-11 mutein, W147A IL-11, is an antagonistic variant of IL-11 that prevents the recruitment of gp130 to the IL-11 receptor complex (Underhill-Day et al, supra 2003) thereby preventing IL-11 signaling. However, W147A IL-11 has the same affinity for IL-11Rα as wild-type IL-11.

There is a role for IL-11 modulators in therapy. The identification of further IL-11 modulators is required.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention relates generally to modified forms of mammalian interleukin-11 (referred to hereinafter as "IL-11 muteins") which exhibit enhanced binding to the IL-11 receptor alpha chain (IL-11Rα). More particularly, the IL-11 muteins of the present invention modulate IL-11 signaling and are therefore useful as Therapeutics in the treatment or prophylaxis of IL-11-mediated conditions. By "modulate" means up-regulate ("agonize") or down-regulate ("antagonize").

Accordingly, the present invention provides an IL-11 mutein comprising an amino acid sequence wherein the amino acid sequence AMSAG (using single letter amino acid code) [SEQ ID NO:23] at position 58 to 62 of wild-type mammalian IL-11 is replaced with the amino acid sequence PAIDY (SEQ ID NO:24) or FMQIQ (SEQ ID NO:25). In one embodiment, the IL-11 mutein is in isolated form although the present invention is not to be so limited.

In another aspect, the IL-11 mutein has, in addition to the mutation at amino acid position 58 to 62 of wild-type mammalian IL-11, a mutation that inhibits its binding to gp130.

In another aspect, the IL-11 mutein has, in addition to the mutation at amino acid position 58 to 62 of wild-type mammalian IL-11, a tryptophan at amino acid position 147 of wild-type IL-11 mutated to inhibit its binding to gp130. Reference to "mutated" in this context includes an amino acid substitution, addition and/or deletion.

Specific IL-11 muteins of the present invention include an IL-11 mutein comprising SEQ ID NO:4, amino acids 10 to 178 of SEQ ID NO:4, amino acids 10 to 175 of SEQ ID NO:4, SEQ ID NO:5, amino acids 10 to 178 of SEQ ID NO:5, amino acids 10 to 175 of SEQ ID NO:5, SEQ ID NO:6, amino acids 10 to 178 of SEQ ID NO:6, amino acids 10 to 175 of SEQ ID NO:6, SEQ ID NO:7, amino acids 10 to 178 of SEQ ID NO:7, amino acids 10 to 175 of SEQ ID NO:7, SEQ ID NO:8, amino acids 10 to 178 of SEQ ID NO:8, amino acids 10 to 175 of SEQ NO:8, SEQ ID NO:13, amino acids 10 to 178 of SEQ ID NO:13 or amino acids 10 to 175 of SEQ ID NO:13.

Other specific IL-11 muteins of the present invention include an IL-11 mutein comprising SEQ ID NO:9, amino acids 10 to 178 of SEQ ID NO:9, amino acids 10 to 175 of SEQ ID NO:9, SEQ ID NO:10, amino acids 10 to 178 of SEQ ID NO:10, amino acids 10 to 175 of SEQ ID NO:10, SEQ ID NO:11, amino acids 10 to 178 of SEQ ID NO:11, amino acids 10 to 175 of SEQ ID NO:11, SEQ ID NO:12, amino acids 10 to 178 of SEQ ID NO:12, amino acids 10 to 175 of SEQ ID NO:12, SEQ ID NO:14, amino acids 10 to 178 of SEQ ID NO:14, amino acids 10 to 175 of SEQ ID NO:14, SEQ ID NO:15, amino acids 10 to 178 of SEQ ID NO:15, amino acids 10 to 175 of SEQ ID NO:15, SEQ ID NO:16, amino acids 10 to 178 of SEQ ID NO:16, amino acids 10 to 175 of SEQ ID NO:16, SEQ ID NO:17, amino acids 10 to 178 of SEQ ID NO:17, amino acids 10 to 175 of SEQ ID NO:17, SEQ ID NO:18, amino acids 10 to 178 of SEQ ID NO:18, amino acids 10 to 175 of SEQ ID NO:18, SEQ NO:19, amino acids 10 to 178 of SEQ ID NO:19, amino acids 10 to 175 of SEQ ID NO:19, SEQ ID NO:20, amino acids 10 to 178 of SEQ ID NO:20, amino acids 10 to 175 of SEQ ID NO:20, SEQ ID NO:21, amino acids 10 to 178 of SEQ ID NO:21 or amino acids 10 to 175 of SEQ ID NO:21.

The present invention also provides a nucleic acid sequence encoding an IL-11 mutein described herein.

In another aspect the present invention provides an IL-11 mutein which is PEGylated.

In another aspect the present invention contemplates a method for the treatment of an IL-11-mediated condition, the method comprising administering to said subject an effective amount of an IL-11 mutein of the present invention.

The present invention is further directed to the use of an IL-11 mutein of the present invention in the manufacture of a medicament for the treatment of an IL-11-mediated condition.

An IL-11-mediated condition includes (a) any condition which benefits or might benefit from increasing treatment with exogenous IL-11 or an IL-11 agonist, for example thrombocytopenia, rheumatoid arthritis, inflammatory bowel disease, infertility, and mucosal damage from chemotherapy and/or radiation therapy; and (b) any condition which benefits or might benefit from treatment with an IL-11 antagonist to reduce or block the activity of endogenous IL-11, for example conditions that result in diminished total bone mass, including metastatic bone cancer, myeloma, Paget's disease of the bone and osteoporosis, and fertility (i.e. an IL-11 antagonist may be used for contraception). In one embodiment, the IL-11 mutein antagonist comprises a substitution of AMSAG at amino acid position 58 to 62 together with a mutation that disrupts binding to gp130. An example of the latter is a mutation at amino acid 147 (e.g. a W147 mutation or a W147A or W147C substitution).

The present invention extends to compositions comprising IL-11 muteins of the present invention and one or more pharmaceutically acceptable carriers and/or diluents and/or excipient.

TABLE 1

Summary of sequence identifiers

| SEQUENCE ID NO: | DESCRIPTION |
|---|---|
| 1 | Human mature IL-11 amino acid sequence |
| 2 | Murine mature IL-11 amino acid sequence |
| 3 | Macaque Mature IL-11 amino acid sequence |
| 4 | Macaque PAIDY IL-11 mutein amino acid sequence |
| 5 | Human PAIDY IL-11 mutein amino acid sequence |
| 6 | Murine PAIDY IL-11 mutein amino acid sequence |
| 7 | Human FMQIQ IL-11 mutein amino acid sequence |
| 8 | Murine FMQIQ IL-11 mutein amino acid sequence |
| 9 | Human PAIDY and W147A IL-11 mutein amino acid sequence |
| 10 | Murine PAIDY and W147A IL-11 mutein amino acid sequence |

TABLE 1-continued

Summary of sequence identifiers

| SEQUENCE ID NO: | DESCRIPTION |
|---|---|
| 11 | Human PAIDY and W147C IL-11 mutein amino acid sequence |
| 12 | Murine PAIDY and W147C IL-11 mutein amino acid sequence |
| 13 | Macaque FMQIQ IL-11 mutein amino acid sequence |
| 14 | Macaque PAIDY and W147A IL-11 mutein amino acid sequence |
| 15 | Macaque PAIDY and W147C IL-11 mutein amino acid sequence |
| 16 | Human FMQIQ and W147A IL-11 mutein amino acid sequence |
| 17 | Murine FMQIQ and W147A IL-11 mutein amino acid sequence |
| 18 | Macaque FMQIQ and W147A IL-11 mutein amino acid sequence |
| 19 | Human FMQIQ and W147C IL-11 mutein amino acid sequence |
| 20 | Murine FMQIQ and W147C IL-11 mutein amino acid sequence |
| 21 | Macaque FMQIQ and W147C IL-11 mutein amino acid sequence |
| 22 | N-terminally tagged Human PAIDY and W147C IL-11 mutein amino acid sequence |
| 23 | Amino acids at position 58 to 62 of wild-type IL-11 |
| 24 | Substitution amino acids at position 58 to 62 of wild-type IL-11 |
| 25 | Substitution amino acids at position 58 to 62 of wild-type IL-11 |

A summary of amino acid single and three letter codes in provided in Table 2.

TABLE 2

Amino Acid Abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalamine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BRIEF DESCRIPTION OF THE FIGURES

FIGS. 1*a* to 1*g* disclose the amino acid sequences of human, murine and monkey IL-11 muteins of the present invention.

DETAILED DESCRIPTION

As used herein, the singular forms “a”, “an” and “the” include plural aspects unless the context clearly dictates otherwise. Thus, for example, reference to “a mutein” includes a single mutein, as well as two or more muteins; reference to “an agent” includes a single agent, as well as two or more agent; reference to “the invention” includes single and multiple aspects of the invention; and so forth.

The term “IL-11” or its full name “interleukin-11” as used herein includes all mature forms of wild-type mammalian IL-11, including murine, macaque and human, and all truncated forms of such IL-11 that retain IL-11 activity, i.e. the ability to bind with IL-11Rα and form a functional receptor complex with gp130. Mature human IL-11 (SEQ ID NO:1) is a 178 amino acid protein (i.e. lacking the 21 amino acid leader sequence of NP_000632, NCBI protein database Accession Number), mature murine IL-11 (SEQ ID NO:2) is a 178 amino acid protein (i.e. lacking the 21 amino acid leader sequence of NP_032376, NCBI protein database Accession Number) and mature macaque IL-11 (SEQ ID NO:3) is a 178 amino acid protein (i.e. lacking the 21 amino acid leader sequence of P20808, NCBI protein database Accession Number).

The term “IL-11 mutein” as used herein refers to an IL-11 in which the amino acid sequence of the wild-type protein has been altered by amino acid substitutions, additions and/or deletions to provide enhanced binding to the IL-11Rα chain to generate an IL-11 mutein agonist or, in the case of an IL-11 mutein antagonist, the amino acid sequence has been further altered by amino acid substitutions, additions and/or deletions to antagonize IL-11 signaling by inhibiting the formation of an IL-11 receptor complex with gp130 while retaining enhanced binding to the IL-11Rα chain. Particularly, the IL-11 mutein is based on a human, macaque or murine IL-II, and more particularly human IL-11. The IL-11 muteins may be further modified, for example to increase their in vivo half life, including for example by the attachment of other elements such as a PEG group. Methods for the PEGylation of peptides are well known in the art. IL-11 muteins may sometimes be referred to as IL-11 mutant proteins or as IL-11 mutants.

The expression “enhanced binding to the IL-11 receptor alpha (IL-11Rα) chain” when used in relation to the IL-11 muteins of the present invention means that the IL-11 mutein exhibits a greater affinity for the IL-11Rα chain than does the corresponding wild-type IL-11 as determined by competition ELISA.

The terms “antagonist”, “agonist” and “compound” may each be used herein to refer to the IL-11 muteins described throughout the specification. The terms also encompass pharmaceutically acceptable and pharmacologically active forms thereof, including salts.

The term “effective amount” as used herein means a sufficient amount of an IL-11 mutein to provide the desired physiological and/or therapeutic effect such as to antagonize IL-11 signaling. In addition, the effect may be an amelioration of the symptoms of an IL-11-mediated condition. Undesirable effects, e.g. side effects, are sometimes manifested along with the desired physiological and/or therapeutic effect; hence, a practitioner balances the potential benefits against the potential risks when determining what is an appropriate "effective amount". The exact amount required will vary from subject to subject, depending on the species, age and general condition of the subject, made of administration and the like. Thus, it may not be possible to specify an exact "effective amount". However, an appropriate "effective amount" in any individual case may be determined by one of ordinary skill in the art using routine experimentation. One of ordinary skill in the art would be able to determine the required amounts based on such factors as the subject's size, the severity of the subject's symptoms, and the particular composition or route of administration selected.

Insofar as one embodiment of the present invention relates to the use of an IL-11 mutein, the effective amount includes from about 10 μg/kg body weight to 20 mg/kg body weight of antibody such as 10, 20, 30, 40, 50, 60, 70, 80, 90, 100 μg/kg body weight, 100, 200, 300, 400, 500, 600, 700, 800, 900, 1000 μg/kg body weight or 2, 3, 4, 5, 6, 7, 8, 9, 10, 11, 12, 13, 14, 15, 16, 17, 18, 19 or 20 mg/kg body weight. Similar amounts are provided for single or combination therapy.

Reference to "a condition mediated by IL-11" or an "IL-11-mediated condition" includes (a) any condition which benefits or might benefit hum increasing treatment with exogenous IL-11 or an IL-11 agonist, for example thrombocytopenia, rheumatoid arthritis, inflammatory bowel disease, infertility, and mucosal damage from chemotherapy and/or radiation therapy; and (b) any condition which benefits or might benefit from treatment with an IL-11 antagonist to reduce or block the activity of endogenous IL-11, for example conditions that result in diminished total bone mass, including metastatic bone cancer, myeloma, Paget's disease of the bone and osteoporosis, and fertility (i.e. an IL-11 antagonist may be used for contraception).

A "pharmaceutically acceptable" carrier and/or diluent is a pharmaceutical vehicle comprised of a material that is not biologically or otherwise undesirable, i.e. the material may be administered to a subject along with the selected mutein without causing any or a substantial adverse reaction. Carriers and diluents may include any and all solvents, dispersion media, coatings, antibacterial and antifungal agents, agents used for adjusting tonicity, buffers, chelating agents, and absorption delaying agents and the like.

Similarly, a "pharmacologically acceptable" salt of a compound as provided herein is a salt that is not biologically or otherwise undesirable.

The terms "treating" and "treatment" as used herein refer to therapeutic treatment. For example, treatment may result in a reduction in severity and/or the frequency of symptoms of the condition, the elimination of symptoms and/or underlying cause of the condition, the prevention of the occurrence of symptoms of the condition and/or their underlying cause and improvement or remediation or amelioration of damage. Hence, the treatment may not result in a "cure" but rather an amelioration of symptoms. In addition, treatment may not commence until an exacerbated event occurs. In this context, the term "prophylaxis" also applies to the prevention or treatment of a likelihood of an event associated with the condition occurring.

The terms "treating" and "treatment" as used herein also refer to the reduction of one or more symptoms or characteristics associated with the conditions.

A "subject" as used herein refers to an animal, preferably a mammal and more preferably a human who can benefit from the pharmaceutical compositions and methods of the present invention. Other preferred mammals are laboratory test animals, examples of which include mice, rats, rabbits, guinea pigs, hamsters, cats and dogs. There is no limitation on the type of animal that could benefit from the presently described pharmaceutical compositions and methods. A subject regardless of whether a human or non-human animal may be referred to as an individual, patient, animal or recipient as well as subject. The methods of the present invention have applications in human medicine and veterinary medicine.

It is shown herein that IL-11 muteins with enhanced binding to the IL-11Rα chain are produced when the amino acid sequence AMSAG (using single letter amino acid code) [SEQ ID NO:23] at positions 58 to 62 of wild-type mammalian IL-11 is replaced with the amino acid sequence PAIDY (SEQ ID NO:24) or FMQIQ (SEQ ID NO:25).

Accordingly, the present invention provides an IL-11 mutein wherein the amino acid sequence AMSAG (SEQ ID NO:23) at positions 58 to 62 of wild-type mammalian IL-11 is replaced with the amino acid sequence PAIDY (SEQ ID NO:24) or FMQIQ (SEQ ID NO:25).

One aspect of present invention provides an IL-11 mutein wherein the amino acid sequence AMSAG at positions 58 to 62 of wild-type human IL-11 (SEQ ID NO:1), murine IL-11 (SEQ ID NO:2) or macaque IL-11 (SEQ ID NO:3) is replaced with the amino acid sequence PAIDY (SEQ ID NO:24).

Another aspect of the present invention provides an IL-11 mutein wherein the amino acid sequence AMSAG at positions 58 to 62 of wild-type human IL-11 (SEQ ID NO:1), murine IL-11 (SEQ ID NO:2) or macaque IL-11 (SEQ ID NO:3) is replaced with the amino acid sequence FMQIQ (SEQ ID NO:25).

In one aspect, an IL-11 mutein of the present invention has a 10-fold, more particularly a 15-fold, and even more particularly a 20-fold higher binding affinity for the IL-11Rα chain than the binding affinity of the corresponding wild-type IL-11.

The inclusion of additional mutations that retain enhanced binding to the IL-11Rα chain but inhibit binding to gp130 provides IL-11 mutein antagonists which compete with IL-11 for binding to the IL-11Rα chain but do not form an IL-11 receptor complex with gp130.

Accordingly, in another aspect the IL-11 mutein may have, in addition to the mutations at amino acid positions 58 to 62 of wild-type mammalian IL-11, an additional mutation that inhibits binding to gp130.

A mutation of the tryptophan (W) residue at amino acid position 147 of wild-type murine IL-11 to alanine (A) is known to inhibit binding of the resulting IL-11 mutant to gp130. It is shown herein that a substitution mutation of the tryptophan residue at amino acid position 147 of wild-type murine IL-11 to cysteine inhibits binding of the resulting IL-11 mutant to gp130. Reference to "mutation" includes an amino acid substitution, addition and/or deletion. A substitution mutation is conveniently described herein as W147A or W147C to denote a change from a tryptophan (W) to an alanine (A) or cysteine (C).

Accordingly, in another aspect the IL-11 mutein may, in addition to the mutation at amino acid positions 58 to 62 of wild-type mammalian IL-11, have the tryptophan at amino acid position 147 of wild-type IL-11 mutated to inhibit its binding to gp130.

In another aspect, the tryptophan at amino acid position 147 of wild-type mammalian IL-II is mutated to an alanine or a cysteine.

In another aspect, the IL-11 mutein may, in addition to the mutation at amino acid positions 58 to 62 of wild-type human IL-11 (SEQ ID NO:1), murine IL-11 (SEQ ID NO:2) or macaque IL-11 (SEQ ID NO:3) have an additional mutation which is inhibit its binding to gp130.

In another aspect, the IL-11 mutein may, in addition to the mutation at amino acid positions 58 to 62 of wild-type human IL-11 (SEQ ID NO:1), murine IL-11 (SEQ ID NO:2) or macaque IL-11 (SEQ ID NO:3) have the tryptophan residue at amino acid position 147 of wild-type mammalian IL-11 mutated to inhibit binding to gp130. In another aspect the tryptophan residue at amino acid position 147 of wild-type mammalian IL-11 is mutated to an alanine or a cysteine.

The present inventors have observed that up to nine N-terminal amino acid residues can be removed from murine IL-11 without loss of activity. Wang et al, *Eur J Biochem.* 269(1): 61-68, 2002, removed ten N-terminal amino acid residues from human IL-11. Barton et al, *J Biol Chem.* 274(9):5755-61, 1999, report that amino acid residue thirteen of murine IL-11 forms part of the site II gp130 binding site and that substitution causes a loss in activity, suggesting that up to the first twelve N-terminal amino acid residues may be removed without significant loss of activity. US Patent Application No. 20070190024 which describes IL-11 muteins that are IL-11 agonists suggests that the first thirteen N-terminal amino acid residues may be removed without loss of activity.

It has also been reported that up to the last three, but not four, amino acid residues may be removed from the C-terminus of human IL-11 without a loss of activity (Czupryn et al, supra 1995).

In another aspect the IL-11 muteins of the present invention may, in addition to the mutations at amino acid positions 58 to 62 of wild-type IL-11, have up to the first thirteen, preferably only up to the first twelve, N-terminal amino acid residues of the corresponding wild-type IL-11 deleted and/or have up to the last three C-terminal amino acid residues of the corresponding wild-type IL-11 deleted.

Specific IL-11 muteins of the present invention include an IL-11 mutein comprising SEQ ID NO:4, amino acids 10 to 178 of SEQ ID NO:4, amino acids 10 to 175 of SEQ ID NO:4, SEQ ID NO:5, amino acids 10 to 178 of SEQ ID NO:5, amino acids 10 to 175 of SEQ ID NO:5, SEQ ID NO:6, amino acids 10 to 178 of SEQ ID NO:6, amino acids 10 to 175 of SEQ ID NO:6, SEQ ID NO:7, amino acids 10 to 178 of SEQ ID NO:7, amino acids 10 to 175 of SEQ ID NO:7, SEQ ID NO:8, amino acids 10 to 178 of SEQ ID NO:8, amino acids 10 to 175 of SEQ ID NO:8, SEQ ID NO:13, amino acids 10 to 178 of SEQ ID NO:13 or amino acids 10 to 175 of SEQ ID NO:13.

Other specific IL-11 muteins of the invention include an IL-11 mutein comprising SEQ ID NO:9, amino acids 10 to 178 of SEQ ID NO:9, amino acids 10 to 175 of SEQ ID NO:9, SEQ 10 NO:10, amino acids 10 to 178 of SEQ ID NO:10, amino acids 10 to 175 of SEQ ID NO:10, SEQ ID NO:11, amino acids 10 to 178 of SEQ ID NO:11, amino acids 10 to 175 of SEQ ID NO:11, SEQ ID NO:12, amino acids 10 to 178 of SEQ ID NO:12, amino acids 10 to 175 of SEQ ID NO:12, SEQ ID NO:14, amino acids 10 to 178 of SEQ ID NO:14, amino acids 10 to 175 of SEQ ID NO:14, SEQ ID NO:15, amino acids 10 to 178 of SEQ ID NO:15, amino acids 10 to 175 of SEQ ID NO:15, SEQ ID NO:16, amino acids 10 to 178 of SEQ ID NO:16, amino acids 10 to 175 of SEQ ID NO:16, SEQ ID NO:17, amino acids 10 to 178 of SEQ ID NO:17, amino acids 10 to 175 of SEQ ID NO:17, SEQ ID NO:18, amino acids 10 to 178 of SEQ ID NO:18, amino acids 10 to 175 of SEQ NO:18, SEQ ID NO:19, amino acids 10 to 178 of SEQ ID NO:19, amino acids 10 to 175 of SEQ ID NO:19, SEQ ID NO:20, amino acids 10 to 178 of SEQ ID NO:20, amino acids 10 to 175 of SEQ ID NO:20, SEQ ID NO:21, amino acids 10 to 178 of SEQ ID NO:21 or amino acids 10 to 175 of SEQ ID NO:21.

IL-11 from monkey (SEQ ID NO:3) and mouse (SEQ ID NO:2) demonstrate considerable identity with the human sequence (SEQ ID NO:1, ~94% and ~87% identity respectively). All these proteins have full cross-species reactivity indicating that their tertiary structures are similar and other functionally critical residues are probably conserved. (Czupryn et al, supra 1995). In view of the cross reactivity of IL-11 from different species it is clear that IL-11 can tolerate some level of amino acid variation and retain IL-11 activity. Accordingly, the IL-11 muteins of the present invention include IL-11 muteins comprising sequences that are at least 85% identical, preferably at least 90% identical and more preferably at least 94% identical to any one of those of SEQ ID NO:4, amino acids 10 to 178 of SEQ ID NO:4, amino acids 10 to 175 of SEQ ID NO:4, SEQ ID NO:5, amino acids 10 to 178 of SEQ ID NO:5, amino acids 10 to 175 of SEQ ID NO:5, SEQ ID NO:6, amino acids 10 to 178 of SEQ ID NO:6, amino acids 10 to 175 of SEQ ID NO:6, SEQ ID NO:7, amino acids 10 to 178 of SEQ ID NO:7, amino acids 10 to 175 of SEQ ID NO:7, SEQ ID NO:8, amino acids 10 to 178 of SEQ ID NO:8, amino acids 10 to 175 of SEQ ID NO:8, SEQ ID NO:9, amino acids 10 to 178 of SEQ ID NO:9, amino acids 10 to 175 of SEQ ID NO:9, SEQ ID NO:10, amino acids 10 to 178 of SEQ ID NO:10, amino acids 10 to 175 of SEQ ID NO:10, SEQ ID NO:11, amino acids 10 to 178 of SEQ ID NO:11, amino acids 10 to 175 of SEQ ID NO:11, SEQ ID NO:12, amino acids 10 to 178 of SEQ ID NO:12, amino acids 10 to 175 of SEQ ID NO:12, SEQ ID NO:13, amino acids 10 to 178 of SEQ ID NO:13, amino acids 10 to 175 of SEQ ID NO:13, SEQ ID NO:14, amino acids 10 to 178 of SEQ ID NO:14, amino acids 10 to 175 of SEQ ID NO:14, SEQ ID NO:15, amino acids 10 to 178 of SEQ ID NO:15, amino acids 10 to 175 of SEQ ID NO:15, SEQ ID NO:16, amino acids 10 to 178 of SEQ ID NO:16, amino acids 10 to 175 of SEQ ID NO:16, SEQ ID NO:17, amino acids 10 to 178 of SEQ ID NO:17, amino acids 10 to 175 of SEQ ID NO:17, SEQ ID NO:18, amino acids 10 to 178 of SEQ ID NO:18, amino acids 10 to 175 of SEQ ID NO:18, SEQ ID NO:19, amino acids 10 to 178 of SEQ ID NO:19, amino acids 10 to 175 of SEQ ID NO:19, SEQ ID NO:20, amino acids 10 to 178 of SEQ ID NO:20, amino acids 10 to 175 of SEQ ID NO:20, SEQ ID NO:21, amino acids 10 to 178 of SEQ ID NO:21 or amino acids 10 to 175 of SEQ ID NO:21.

The present invention also provides nucleic acid sequences encoding the IL-11 muteins described herein. A nucleic acid sequence or nucleic acid includes a polynucleotide or nucleic acid molecule.

The present invention employs conventional molecular biology, microbiology, and recombinant DNA techniques to modify wild-type IL-11 nucleic acid sequences to produce the IL-11 muteins of the present invention. The techniques are well known in the art and are described in various publications, such as Sambrook, Fritsch & Maniatis, *Molecular Cloning: A Laboratory Manual*, Second Edition, Cold Spring Harbor Laboratory Press, Cold Spring Harbor, N.Y., 1989; *DNA Cloning: A Practical Approach*, Volumes I and II (D. N. Glover ed. 1985), Ausubel, et al. (eds.), *Current Protocols in Molecular Biology*, John Wiley & Sons, Inc., 1994, Sidhu et al, *Methods Enzymol* 328:333-363, 2000) and Kunkel et al, *Methods Enzymol* 204: 1991.

The terms "polynucleotide", "nucleic acid" or "nucleic acid molecule" refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

The terms "polynucleotide sequence", "nucleic acid sequence" or "nucleotide sequence" refer to a series of nucleotide bases (also referred to as "nucleotides") in a nucleic acid, such as DNA or RNA, and means any chain of two or more nucleotides.

The terms "coding sequence" or a sequence "encoding" an expression product, such as a RNA, polypeptide, protein, or enzyme, is a nucleotide sequence that, when expressed, results in the production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

The term "amplification" of nucleotide sequence as used herein may denote the use of the polymerase chain reaction (PCR) to increase the concentration of a particular nucleotide sequence within a mixture of nucleotide sequence sequences. Saiki, et al, *Science* 239:487, 1988 provide a description of PCR.

The term "oligonucleotide" refers to a nucleic acid, generally of at least 10, particularly at least 15, and more particularly at least 20 nucleotides, particularly no more than 100 nucleotides that may be hybridizable to a genomic DNA molecule, a cDNA molecule, or an mRNA molecule encoding a gene, mRNA, cDNA, or other nucleic acid of interest. Oligonucleotides can be labeled for example, by incorporation of $32^P$-nucleotides, $3^H$-nucleotides, $14^C$-nucleotides, $35^S$-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

The sequence of any nucleic acid (for example, a nucleic acid encoding a wild-type IL-11 protein or an IL-11 mutein) may be sequenced by any method known in the art such as by chemical sequencing or enzymatic sequencing. "Chemical sequencing" of DNA may be done by the method of Maxam and Gilbert (*Proc. Natl. Acad. Sci. USA* 74(2): 560-564, 1977), in which DNA is randomly cleaved using individual base-specific reactions. "Enzymatic sequencing" of DNA may be done by the method of Sanger (Sanger et al., *Proc. Natl. Acad. Sci. USA* 74(12):5463 5467, 1977).

Nucleic acids of the present invention may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is a DNA regulatory region capable of binding an RNA polymerase in a cell and initiating transcription of a coding sequence. A promoter sequence is generally bounded at its 3' terminus by the transcription initiation site and extends upstream in the 5' direction to include the minimum number of bases or elements necessary to initiate transcription at any level. A transcription initiation site as well as protein binding domains (consensus sequences) responsible for the binding of RNA polymerase may be found within the promoter sequence. The promoter may be operably associated with other expression control sequences, including enhancer and repressor sequences or with a nucleic acid of the invention. Promoters which may be used to control gene expression include, but are not limited to, the cytomegalovirus (CMV) promoter (U.S. Pat. Nos. 5,385,839 and 5,168,062) and the SV40 early promoter region (Benoist, et al, *Nature* 290:304-310, 1981).

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The terms "express" and "expression" mean allowing or causing the information in a gene, RNA or DNA sequence to be converted into a product; for example, producing a protein by activating the cellular functions involved in transcription and translation of a nucleotide sequence. A DNA sequence is expressed in or by a cell to form an "expression product" such as RNA (such as mRNA) or a protein (such as an IL-11 mutein). The expression product itself may also be said to be "expressed" by the cell.

The terms "vector", "cloning vector" and "expression vector" mean the vehicle (such as a plasmid) by which a DNA or RNA sequence can be introduced into a host cell, so as to transform the host and, optionally, promote expression and/or replication of the introduced sequence.

The term "transfection" or "transformation" means the introduction of a nucleic acid into a cell. These terms may refer to the introduction of a nucleic acid encoding an IL-11 mutein into a cell. The introduced gene or sequence may be called a "clone". A host cell that receives the introduced DNA or RNA has been "transformed" and is a "transformant" or a "clone". The DNA or RNA introduced to a host cell can come from any source, including cells of the same genus or species as the host cell, or cells of a different genus or species.

The term "host cell" means any cell of any organism that is selected, modified, transfected, transformed, grown, or used or manipulated in any way, for the production of a substance by the cell, for example the expression or replication, by the cell, of a gene, a DNA or RNA sequence, a protein or an enzyme.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

The present invention contemplates any slight modifications of the amino acid or nucleotide sequences which corresponds to or encodes the IL-11 muteins of the sequences described herein excluding modifications that would change the amino acid segment corresponding to amino acids 58 to 62 of wild-type mammalian IL-11 which segment will have the sequence PAIDY (SEQ ID NO:24) or FMQIQ (SEQ ID NO:25). In particular, the present invention contemplates sequence conservative variants of the nucleic acids which encode the IL-11 muteins of the invention. "Sequence-conservative variants" of a polynucleotide sequence are those in which a change of one or more nucleotides in a given codon results in no alteration in the amino acid encoded at that position. Function-conservative variants of the IL-11 muteins of the invention are also contemplated by the present invention. "Function-conservative variants" are those in which one or more amino acid residues in a protein have been changed without altering the overall conformation and function of the protein, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, praline, tyrosine, phenylalanine, tryptophan and methionine; acidic amino acids which may be interchangeable include aspartic acid and glutamic acid and basic amino acids which may be interchangeable include histidine, lysine and arginine. Preferably, function-conservative variants of the IL-11 muteins of the invention have less than 20, more preferably less than 15, more preferably less than 10 amino acid changes.

Also included in the present invention are IL-11 muteins wherein the amino acid sequence AMSAG (SEQ ID NO:23) at positions 58 to 62 of wild-type mammalian IL-11 is replaced with the amino acid sequence PAIDY (SEQ ID NO:24) or FMQIQ (SEQ ID NO:25) and comprising amino acid sequences which are at least 85% identical, particularly at least 90% identical, more particularly at least 94% identical (e.g. 94%, 95%, 96%, 97%, 98%, 99%) to the amino acid sequences described herein when the comparison is performed by a BLAST algorithm wherein the parameters of the algorithm are selected to give the largest match between the respective sequences over the entire length of the respective reference sequences.

Sequence identity refers to exact matches between the amino acids of two sequences which are being compared.

Descriptions for BLAST algorithms can be found in the following references which herein incorporated by reference: BLAST ALGORITHMS: Altschul et al, *J. Mol. Biol.* 215: 403-410, 1990; Altschul et al, *Nucleic Acids Res.* 25:3389-3402, 1997; Altschul, *J. Mol. Biol.* 219:555-565, 1991.

The IL-11 muteins of the present invention may be produced recombinantly, for example, in an *E. coli* expression system. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation and encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

In one aspect, the present invention provides a method for the production of an IL-11 mutein of the invention, said method comprising cloning a nucleic acid sequence encoding an IL-11 mutein into an appropriate vector, transforming a host cell line with the vector, and culturing the transformed host cell line under conditions suitable for the expression of the antibodies of the present invention.

Vectors available for cloning and expression in host cell lines are well known in the art, and include but are not limited to vectors for cloning and expression in mammalian cell lines, vectors for cloning and expression in bacterial cell lines and vectors for cloning and expression insect cell lines. The IL-11 muteins can be recovered using standard protein purification methods.

In another aspect, the present invention provides nucleic acid sequences encoding IL-11 muteins having the amino acid sequences shown in SEQ ID NOs:5 to 12.

In still a further aspect, the present invention provides host cell lines transformed with the vectors of the present invention. Host cell lines include, but are not limited to, bacterial cells, such as *E. coli* and mammalian cell lines.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9. cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

The IL-11 muteins can be recovered from the culture medium using standard protein purification methods. Further, expression of IL-11 muteins of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

It is likely that the IL-11 muteins expressed by different cell lines or in transgenic animals will have different glycosylation from each other. However, all IL-11 muteins encoded by the nucleic acid molecules provided herein, or comprising the amino acid sequences provided herein are part of the invention, regardless of the glycosylation of the IL-11 muteins.

In a further aspect, the present invention provides a human or murine IL-11 muteins that have been further modified to enhance their pharmacokinetic properties and half life in vivo. Modifications include PEGylation with polyethylene glycol, (Clark et al, *J Biol Chem* 271(36):21969-77, 1996), fusions to large long lived proteins such as albumin (Yeh et al, *Proc Natl Acad Sci USA.* 89(5):1904-8, 1992) or the Fc portion of an Ig (Ashkenazi and Chamow, *Curr Opin Immunol.* 9(4:195-200, 1997) and the introduction of glycosylation sites (Keyt et al, *Proc Natl Acad Sci USA.* 91(9):3670-4, 1994).

An aspect of the invention provides IL-11 mutein antagonists that are PEGylated.

One aspect of the present invention provides IL-11 muteins having the amino acid sequences of SEQ ID NO:11, amino acids 10 to 178 of SEQ ID NO:11, amino acids 10 to 175 of SEQ ID NO:11, SEQ ID NO:12, amino acids 10 to 178 of SEQ ID NO:12 amino acids 10 to 175 of SEQ ID NO:12, SEQ ID NO:15, amino acids 10 to 178 of SEQ ID NO:15, amino acids 10 to 175 of SEQ ID NO:15, SEQ ID NO:19, amino acids 10 to 178 of SEQ ID NO:19, amino acids 10 to 175 of SEQ ID NO:19, SEQ ID NO:20, amino acids 10 to 178 of SEQ ID NO:20, amino acids 10 to 175 of SEQ ID NO:20, SEQ ID NO:21, amino acids 10 to 178 of SEQ ID NO:21 or amino acids 10 to 175 of SEQ ID NO:21 that are PEGylated.

The IL-11 muteins of the invention may be conveniently supplied in compositions suitable for pharmaceutical use. Such compositions are another aspect of the present invention.

Administration may be systemic or local. Systemic administration is particularly useful. Reference to "systemic administration" includes intra-articular, intravenous, intraperitoneal, and subcutaneous injection, infusion, as well as administration via oral, rectal and nasal routes, or via inhalation.

Compositions suitable for systemic use include sterile aqueous solutions (where water soluble), sterile powders for the extemporaneous preparation of sterile injectable solutions, and sterile powders for inhalation. It must be stable under the conditions of manufacture and storage and must be preserved against the contaminating action of microorganisms such as bacteria and fungi. The carrier can be any pharmaceutically acceptable carriers and/or diluent, for example, water, ethanol, polyol (for example, glycerol, propylene glycol and liquid polyethylene glycol, and the like), suitable mixtures thereof and vegetable oils. The proper fluidity can be maintained, for example, by the use of superfactants. Various anti-bacterial and anti-fungal agents, for example, parabens, chlorobutanol, phenol, sorbic acid, thirmerosal and the like may be included. In many cases, it will be preferable to include agents to adjust tonicity, for example, sugars or sodium chloride. Prolonged absorption of the injectable compositions can be brought about by the use in the compositions of agents delaying absorption, for example, aluminum monostearate and gelatin.

Sterile solutions are prepared by incorporating the active in the required amount in the appropriate solvent and optionally with other active ingredients and excipients as required, followed by filtered sterilization or other appropriate means of sterilization, in the case of sterile powders, suitable methods of preparation include vacuum drying and the freeze-drying technique which yield a powder of active ingredient plus any additionally desired ingredient which can be made at an appropriate particle size.

When the active is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like.

Dosage regimens may be adjusted to provide the optimum desired response (e.g. a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the antagonist, employed in the pharmaceutical composition, at levels lower than that required in order to achieve the desired therapeutic effect and gradually increase the dosage until the desired effect is achieved. In general, a suitable dose of a composition of the invention may be that amount of the compound which is the lowest dose effective to produce a therapeutic effect.

For therapeutic applications, the IL-11 muteins of the present invention or compositions containing those muteins are administered to a mammal, preferably a human, in a pharmaceutically acceptable dosage form such as those discussed above, including those that may be administered to a human intravenously as a bolus or by continuous infusion over a period of time.

In one aspect, the present invention contemplates a method for the treatment of a condition mediated by IL-11, the method comprising administering to said subject an effective amount of an IL-11 mutein of the present invention.

The IL-11 muteins of the present invention that are agonists, and compositions comprising such muteins, may be used in a method for the treatment of IL-11-mediated conditions where IL-11 exerts a positive effect.

The IL-11 muteins of the present invention that are antagonists and compositions comprising such muteins may be used in a method for the treatment of IL-11-mediated conditions where IL-11 exerts a negative effect.

The IL-11 muteins of the present invention and compositions comprising such muteins may be used in a method of manufacture of a medicament for the treatment of IL-11-mediated conditions.

Particular IL-11 mutein antagonists of the present invention are IL-11 muteins having the amino acid sequences of SEQ ID NO:11, amino acids 10 to 178 of SEQ ID NO:11, amino acids 10 to 175 of SEQ ID NO:11, SEQ ID NO:12, amino acids 10 to 178 of SEQ ID NO:12 amino acids 10 to 175 of SEQ ID NO:12, SEQ ID NO:15, amino acids 10 to 178 of SEQ ID NO:15, amino acids 10 to 175 of SEQ ID NO:15, SEQ ID NO:19, amino acids 10 to 178 of SEQ ID NO:19, amino acids 10 to 175 of SEQ ID NO:19, SEQ ID NO:20, amino acids 10 to 178 of SEQ ID NO:20, amino acids 10 to 175 of SEQ ID NO:20, SEQ ID NO:21, amino acids 10 to 178 of SEQ ID NO:21 or amino acids 10 to 175 of SEQ ID NO:21 and which may be PEGylated. Particularly PEGylation is via attachment to the cysteine residue corresponding to position 147 of SEQ ID NO's 11, 12, 15, 19, 20 or 21.

The invention further contemplates the use of an IL-11 mutein in the manufacture of a medicament for the treatment of an IL-11-mediated condition.

The present invention is further described by the following non-limiting Examples.

Example 1

IL-11 Mutant Proteins

A. Recombinant Production of Soluble IL-11 Mutant Proteins

The IL-11 mutants 1.21 (SEQ ID NO:10), 1B.382 (SEQ ID NO:17) and mIL-11-W147A were cloned into a modified version of the pET15b vector (Novagen Cat #69661-3). The pET15b vector was modified by replacing the thrombin cleavage site and multiple cloning sites with AscI and EcoRI restriction sites, and by inserting an M13 origin of replication so the vector could be used as a phagemid.

The corresponding N-terminal hexahistidine-tagged proteins were expressed in the *E. coli* strain BL21-CodonPlus [Registered trade mark] (DE3)-RIL *E. coli* (Strategene cat #230245). Typically, 400 mL shake-flask cultures in super-broth containing 2% v/v glucose and 100 μg/mL ampicillin were grown to an optical density (600 nm) of 0.5. Protein expression was then induced by the addition of isopropyl-β-

D-thiogalactopyranoside to a final concentration of 200 uM, and the cultures were incubated with shaking at 37° C. for a further 4 hours. The recombinant proteins were purified from the bacterial cells (lysed in 7 M guanidinium hydrochloride) using immobilized nickel ion affinity chromatography, and refolded by dialysis into PBS. The refolded samples were further dialyzed against 0.15% aqueous trifluoroacetic acid. In some cases samples were also purified by reverse phase HPLC using acetonitrile gradients in 0.15% v/v trifluoroacetic acid before lyophilization. Samples were reconstituted in a small volume of water prior to dilution with buffer.

The affinity of the selected IL-11 mutants for IL-11Rα was determined in a competition ELISA experiment. 96 well plates coated with mIL-11 Rα-Fc were incubated with a constant sub-saturating amount of the phage displayed IL-11 variants in the presence of different concentrations of soluble IL-11 proteins. After incubation for 2 hours at room temperature, the plates were washed and bound phage were then labeled with an anti-M13 polyclonal antibody conjugated to horseradish peroxidase. After the removal of excess antibody by washing with PBS containing 0.05% Tween 20, TMB substrate was added to each well and incubated for 10 minutes before the reaction was quenched by the addition of 2M phosphoric acid. Absorbance at 450 nm was then determined for each well by analysis on a microtitre plate reader.

The W147A mutation has no effect on IL-11Rα binding but does prevent the recruitment of gp130 to the IL-11 receptor complex (Underhill-Day et al, 2003 supra) thereby preventing IL-11 signaling. W147A IL-11 is an antagonistic variant of IL-11.

Clear differences were observed between the affinities of the mIL-11-W147A and mutant proteins for binding to IL-11Rα-Fc. Relative to W147A IL-11, clone 1.21 (SEQ ID NO:10) bound to IL-11Rα with a 20-fold higher affinity, while clone 1B.382 (SEQ ID NO:17) also bound IL-11Rα with a 20-fold higher affinity.

B. In Vitro Activity of Antagonist

An IL-11 responsive Ba/F3 cell line was generated to test the ability of the mutant IL-11 proteins to block IL-11 bioactivity. Ba/F3 cells, a murine pro B-lymphocyte cell line which does not normally express IL-11Rα or gp130 nor proliferate in response to IL-11 were stably transfected with constructs encoding wild-type murine IL-11Rα and the co-receptor murine gp130 and selected by growth in media containing IL-11. Clonal cell lines were derived by limit dilution cloning. A number of stably transfected clones were analyzed for their dose-responsive proliferation (using a MTT assay) when cultured in the presence of IL-11 and one was selected for further work.

IL-11 responsive Ba/F3 cells stably transfected with murine IL-11Rα/gp130 were seeded at $3\times10^4$ cells/well in 50 uL of Dulbecco's modified Eagle's medium containing 10% (v/v) fetal calf serum and increasing concentrations of mutant IL-11 proteins in the presence of a fixed, submaximal concentration of murine IL-11 (50 pM) in a total volume of 100 uL/well. After incubation for 48 hours, proliferation was measured colorimetrically at 570 nm using 3-(4,5-dimethylthiazol-2-yl)-2,5-diphenyl tetrazolium bromide (MTT; Sigma-Aldrich). Assays were always performed in duplicate and mean values for each assay point were then plotted.

W147A IL-11 has been previously characterized as an antagonist of IL-11 bioactivity (Underhill-Day et al, 2003 supra). When IL-11R.alpha./gp130 Ba/F3 cells were stimulated with a sub-maximal dose of IL-11, W147A IL-11 was able to inhibit cell proliferation in a dose-dependent manner. Several of the mutant IL-11 proteins were assayed for their ability to inhibit IL-11-induced proliferation and compared to W147A IL-11 (Table 3). The mutant IL-11 proteins were significantly more potent at blocking the proliferation induced IL-11 as measured in a standard MTT assay. Clones 1.21 (SEQ ID NO:10) and 1B.382 (SEQ ID NO:17) were both 20 to 30-fold more potent antagonists of IL-11 than W147A IL-11.

Example 2

PEGylated IL-11 Muteins

Production of PEGylated IL-11 muteins

The mature protein sequence of murine IL-11 contains an amino acid sequence that can be cleaved by thrombin resulting in the removal of the first nine amino acids. A comparison of the IL-11 mutein 1.21 (SEQ ID NO:10) with and without the first nine amino acids showed identical activity and indicated that the first nine residues of murine IL-11 are not required for IL-11Rα, binding. The internal thrombin site was optimized by site directed mutagenesis to allow for efficient cleavage by mutation of residues 6 and 7 to Leu (L) and Val (V), respectively. For large scale production of the PEGylated IL-11 mutein of amino acids 10-178 of SEQ ID NO:12 the amino-terminal His-tag and the first nine residues of the modified mIL-11 sequence were removed by thrombin digestion.

For cleavage of the N-terminal hexahistidine tag, lyophilized samples of the relevant IL-11 mutein protein were re-suspended in thrombin cleavage buffer (150 mM NaCl, 2.5 mM $CaCl_2$, 20 mM Tris.HCl pH 8.4) at a concentration of 0.5 mg/mL and treated with 5 units of thrombin/mg protein for 4 hours at room temperature. Under these conditions, thrombin efficiently cleaves murine derived IL-11 mutein at the optimized internal site between residues $Arg^9$-$Val^{10}$ and the thrombin digested samples have an N-terminal sequence of $Val^{10}$-$Ser^{11}$-$Ser^{12}$. Following treatment with thrombin the cleaved samples were purified by reverse phase HPLC as previously described.

Site-Specific PEGylation

A limitation to the in vivo use of small proteins is their rapid clearance from circulation. One of the main routes of clearance is via filtration through the kidney, the efficiency of which is inversely proportional to the molecular weight. One strategy for reducing the in vivo clearance rate of small proteins is through chemical modification with polyethylene glycol (Tsutsumi et al, *Thjromb. Haemost.* 77.1:168-73, 1997), however, this can reduce or even eliminate the activity of a protein if attached at an inappropriate site.

To improve the potential pharmacokinetic properties of a mutant IL-11 protein for in vivo use, a strategy was designed for site-specific modification of the mutant IL-11 proteins with a 40 kDa polyethylene glycol moiety. The absence of cysteine with the sequence of IL-11 was exploited to introduce a single unique Cys residue at position 147 by site directed mutagenesis. This provided a chemically reactive sidechain which could be site-specifically modified with a maleimide-derivatized PEG reagent. Moreover, the site of PEG attachment corresponds to site III on the surface of IL-11, and should not interfere with binding of the mutant IL-11 proteins to IL-11Rα, or to the gp130 molecule which binds to the site II surface.

Modified forms of the mutant IL-11 proteins were generated containing a W147C mutation and the optimized internal thrombin site described above. The proteins were expressed in *E. coli* and purified and refolded as described in Example 1. The N-terminal His-tag and the first 9 N-terminal amino acids were then cleaved with thrombin as described above. The thrombin-treated samples were purified as described in Example 1 except that the samples was adjusted to pH 8.0 and reduced with 5 mM DTT prior to refolding in PBS containing 2 mM EDTA and 2 mM DTT.

Mutant IL-11 proteins containing an engineered Cys residue at the position corresponding to position 147 of SEQ ID NO:12 were then modified with 40 kDa maleimide-derivatized polyethylene glycol. Briefly, lyophilized thrombin-treated mutant IL-11 proteins were resuspended at a concentration of 5 mg/mL in 1 mM aqueous acetic acid containing 5 mM tris(2-carboxyethyl)phosphine, and mixed with 4 volumes of 12.5 mg/mL mPEG2-maleimide (Nektar Therapeutics cat #2D3YOTO1) in PBS. Reactions were incubated for 16 hours at room temperature and protein-PEG conjugates were then separated from unconjugated components by cation exchange chromatography on an SP Sepharose column, using a NaCl gradient in 20 mM sodium acetate, pH 5.5 buffer. Fractions containing the PEGylated products were pooled, dialyzed against 5 mM ammonium acetate buffer, pH 5.5, and then lyophilized.

A modified form of clone 1.21, containing a W147C mutation and an optimized internal thrombin site, was expressed in *E. coli*, and purified and refolded as described. The N-terminal His-tag and 9 amino acid residue fragment were cleaved with thrombin and then site-specifically PEGylated at Cys147 (where Cys147 is the position corresponding to position 147 of SEQ ID NO:12). Excess PEG reagent was removed by ion exchange chromatography. Analysis of the PEGylated and truncated modified form of clone 1.21 (referred to herein as Δ1.21) by SDS-PAGE showed a shift in apparent molecular weight consistent with attachment of a single 40 kDa PEG moiety.

The activity of Δ1.21 was tested in the IL-11Rα binding ELISA and the Ba/F3 cell assay, and compared to the activity of non-PEGylated 1.21 (containing Ala at position 147) and with non-PEGylated W147A IL-11. In both assays, the activity of Δ1.21 was reduced relative to non-PEGylated 1.21. IL-11Rα binding affinity was reduced approximately 5-fold, whilst the ability of Δ1.21 to antagonize IL-11-induced Ba/F3 cell proliferation was reduced approximately 10-fold. Moderate decreases in potency are commonly observed for PEGylated proteins and often result from a decrease in the rate of association between the protein and its target receptor. Despite the decrease in potency, Δ1.21 was nevertheless more potent than non-PEGylated W147A IL-11 in both assays.

Example 3

In Vivo Half Life

Female C57BL/6J mice (around 8 weeks old and 20+/−2 g) were used to determine the in vivo half life of PEGylated mutein (Δ1.21) and non-PEGylated thrombin cleaved mutein 1.21 (i.e. amino acids 10-178 of SEQ ID NO:10). Each mouse received 1 IP injection. Mice were injected with the thrombin cleaved mutein 1.21 at a dose of 1 mg/kg (20 ug per animal) or with an equivalent molar dose of Δ1.21 at a dose of 3.2 mg/kg (64 ug per animal). At an appropriate time following the IP injection, the mice were killed by $CO_2$ inhalation, followed by cervical dislocation, and blood collected by cardiac puncture. Sera was separated from the blood by incubation at 37° C. for 1 hour and then overnight at 4° C. before centrifugation to pellet the red blood cells. Blood was collected at 5 minute, 10 minutes, 30 minutes, 1 hour, 2 hours and 5 hours from mice injected with thrombin cleaved mutein 1.21 and at 10 minutes, 1 hour, 2 hours, 6 hours, 24 hours, 48 hours and 72 hours from mice injected with Δ1.21. A total of 4 mice were used for each time point.

The concentration of the thrombin cleaved mutein 1.21 was quantitated using a capture ELISA. Briefly, ELISA plates were coated with 2 μg/ml mIL-11Rα-Fc (50 μl/well) [R&D systems] overnight at 4° C. in PBS and the plates were then blocked with PBS containing 5% w/v skim milk (200 μl/well) for 2 hours at room temperature. After washing the blocked plates with PBS containing 0.05% v/v Tween 20, serum samples were serially diluted in Tris buffered saline containing 1% w/v BSA and 0.05% v/v Tween 20 (TBS+BT) and added to the plates (100 μl/well). The plates were incubated overnight at 4° C. Plates were washed with PBS containing 0.05% v/v Tween 20 after the overnight binding of the mutein in the serum to the mIL-11Rα-Fc coated on the plate, and then incubated with polyclonal biotinylated anti-mIL-11 (50 μl/well) [R&D systems, cat#BAF418] at 0.3 μg/ml in TBS+BT for 2 hours at room temperature. After washing in PBS containing 0.05% v/v Tween 20 the plate was incubated with streptavidin-HRP (Sigma) [50 μl/well] diluted 1000-fold in TBS+BT and incubated for 1 hour at room temperature. After washing in PBS containing 0.05% v/v Tween 20 TMB substrate was added to each well (100 μl/well) and after 10 minutes incubation the reaction was stopped with 2M phosphoric acids (50 μl/well) and the plate read at a wavelength of 450 nm using a microtitre plate reader. A standard curve was generated for both thrombin cleaved mutein 1.21 and Δ1.21 using known concentrations of proteins. These standard curves were then used to convert the ELISA data into nM values for thrombin cleaved mutein 1.21 and Δ1.21 contained in the serum.

PEGylation of the mutein clearly improved the half-life. The highest concentration of unPEGylated thrombin cleaved mutein 1.21 in the serum was seen at the earliest time point of 5 minutes after administration and was in continual decline. Only minimal amounts of unPEGylated thrombin cleaved mutein 1.21 remained in the serum 5 hours after administration and was estimated to have a half-life of less than 1 hour. By comparison the highest concentration of Δ1.21 in the serum was seen at 6 hours post administration and was still present in measurable concentrations 72 hours post injection. The half-life of the Δ1.21 was estimated to be approximately 24 hours.

Example 4

PEGylated Human IL-11 Mutein

A PEGylated human IL-11 mutein was prepared based on SEQ ID NO:11. This was expressed purified and refolded as described and then site-specifically PEGylated at Cys147 (numbering based on SEQ ID NO:11) using the general approach described above for the murine IL-11 mutein. Human IL-11 does not contain an internal thrombin site so the first 9 amino acids of the human IL-11 sequence as well as a tag sequence from the vector were retained to provide the mutein of SEQ ID NO:22.

The PEGylated human IL-11 mutein of SEQ ID NO:22 had equivalent activity to the pegylated mouse IL-11 mutein Δ1.21 described above in both ELISA and Ba/F3 assays.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

Cell assay data

| Clone ID | Sequence | $IC_{50}$ (nM) | $IC_{50}$ (mutant)/ $IC_{50}$(wild-type*) |
|---|---|---|---|
| wild-type* | | 14 | 1.0 |
| 1.21 | $^{58}$P-A-I-D-Y$^{62}$ | 0.54 | 26 |
| 1B.382 | $^{58}$F-M-Q-I-Q$^{62}$ | 0.49 | 29 |

BIBLIOGRAPHY

Altschul et al, *J. Mol. Biol.* 215:403-410, 1990

Altschul, *J. Mol. Biol.* 219:555-565, 1991

Altschul et al, *Nucleic Acids Res.* 25:3389-3402, 1997

Ashkenazi and Chamow, *Curr Opin Immunol.* 9(2):195-200, 1997

Ausubel, et al. (eds.), *Current Protocols in Molecular Biology*, John Wiley & Sons, Inc., 1994

Barton et al, *J Biol Chem.* 274(9):5755-61, 1999

Barton et al, *J Biol Chem* (2000) 275:36197-36203, 2000

Baumann and Schendel, *J Biol Chem* 266:20424-20427, 1991

Benoist, et al, *Nature* 290:304-310, 1981

Bilinski et al, *Genes Dev* 12:2234-2243, 1998

Brakenhoff et al, *J Biol Chem* 269:86-93, 1994

Chang et al, *Blood Cells Mol Dis* 22(1):57-67, 1996

Clark et al, *J Biol. Chem.* 271(36):21969-77, 1996

Cunningham and Wells, *Science* 244:1081-1085, 1989

Czupryn et al, *J. Biol. Chem.* 270 (2): 978-985, 1995

Czupryn et al, *Ann. N.Y. Acad. Sci.* 762:152-164, 1995

Dimitriadeis et al, *Mol Hum Reprod.* 6(10): 907-914, 2000

Du et al, *J Cell Physiol* 168:362-372, 1996

Ehlers et al, *J Biol Chem* 270:8158-8163, 1995

Girasole et al, *J Clin Invest* 93:1516-1524, 1994

Harmegnies et al, *Biochem* 375(1):23-32, 2003

Herrlinger et al, *Am J Gastroenterol* 101(4):793-797, 2006

Heymann and Rousselle, *Cytokine* 12 (10):1455-1468, 2000

Hudson et al, *J Biol Chem* 271:11971-11978, 1996

Hughes et al, *Calcif Tissue Int* 53:362-364, 1993

Keyt et al, *Proc Natl Acad Sci USA.* 91(9):3670-4, 1994

Kunkel, *Proc. Natl. Acad. Sci. USA* 82.2:488-92, 1985

Kunkel et al, *Methods Enzymol* 204: 1991

Lopez-Valpuesta et al, *Neuropharmacology* 33:989-994, 1994

Maier et al, *J Biol Chem* 268:21527-21532, 1993

Maxam and Gilbert, *Proc. Natl. Acad. Sci. USA* 74(2): 560-564, 1977

Mehler et al, *Nature* 362:62-65, 1993

Miyadai et al, *Biosci. Biotechnol. Biochem* 60.3:541-542, 1996

Ohsumi et al, *FEBS Lett* 288:13-16, 1991

Ohsumi et al, *Biochem Mol Biol Int* 32:705-712, 1994

Redlich et al, *J Immunol* 157:1705-1710, 1996

Robb et al, *Nat Med* 4:303-308, 1998

Saggio et al, *Embo J* 14; 3045-3054, 1995

Saiki, et al, *Science* 239:487, 1988

Sambrook, Fritsch & Maniatis, *Molecular Cloning: A Laboratory Manual*, Second Edition (1989) Cold Spring Harbor Laboratory Press, Cold Spring Harbor, N.Y.; *DNA Cloning: A Practical Approach*, Volumes I and II, D. N. Glover ed. 1985

Sanger, et al, *Proc. Natl. Acad. Sci. USA* 74(12):5463 5467, 1977

Savino et al, *Embo J* 13:5863-5870, 1994

Sidhu et al, *Methods Enzymol* 328:333-363, 2000

Tacken et al, *Eur. J. Biochem.* 265.2:645-655, 1999

Tepler et al, *Blood* 87(9):3607-3614, 1996

Trepicchio et al, *J Clin Invest* 104:1527-1537, 1999

Tsutsumi et al, *Thjromb. Haemost.* 77.1:168-73, 1997

Underhill-Day et al, *Endocrinology* 144; 3406-3414, 2003

Wang et al, *Eur J Biochem.* 269(1):61-68, 2002

Yeh et al, *Proc Natl Acad Sci USA.* 89(5):1904-8, 1992

The invention claimed is:

1. A human IL-11 mutein comprising:

i. an amino acid sequence that has at least 95% identity to amino acids 10 to 175 of SEQ ID NO:11; and ii. the amino acid sequence PAIDY (SEQ ID NO:24) at the amino acid positions of said mutein that correspond to positions 58 to 62 of SEQ ID NO:11.

2. The human IL-11 mutein of claim 1 wherein the mutein comprises at least one amino acid substitution, addition or deletion, relative to the amino acid sequence of SEQ ID NO:11, outside of positions 58 to 62 of SEQ ID NO:11.

3. The human IL-11 mutein of claim 1 further comprising an amino acid substitution of the cysteine (C) at amino acid position 147 of SEQ ID NO:11 to alanine (A) or tryptophan (W).

4. The human IL-11 mutein of claim 1 which IL-11 mutein is PEGylated.

5. A pharmaceutical composition comprising the IL-11 mutein of claim 1 and further comprising one or more pharmaceutically acceptable carriers, diluents and/or excipients.

6. A human IL-11 mutein comprising:

i. an amino acid sequence that has at least 95% identity to amino acids 10 to 178 of SEQ ID NO:11; and ii. the amino acid sequence PAIDY (SEQ ID NO:24) at the amino acid positions of said mutein that correspond to positions 58 to 62 of SEQ ID NO:11.

7. The human IL-11 mutein of claim 2 wherein the at least one amino acid substitution, addition or deletion inhibits or reduces binding of the mutein to gp130.

8. The human IL-11 mutein of claim 6 wherein the mutein comprises at least one amino acid substitution, addition or deletion, relative to the amino acid sequence of SEQ ID NO:11, outside of positions 58 to 62 of SEQ ID NO:11.

9. The human IL-11 mutein of claim 8 wherein the at least one amino acid substitution, addition or deletion inhibits or reduces binding of the mutein to gp130.

10. The human IL-11 mutein of claim 6 further comprising an amino acid substitution of the cysteine (C) at amino acid position 147 of SEQ ID NO:11 to alanine (A) or tryptophan (W).

11. The human IL-11 mutein of claim 6 which IL-11 mutein is PEGylated.

12. A pharmaceutical composition comprising the IL-11 mutein of claim 6 and further comprising one or more pharmaceutically acceptable carriers, diluents and/or excipients.

* * * * *